(12) United States Patent
Lowry

(10) Patent No.: US 6,828,102 B2
(45) Date of Patent: Dec. 7, 2004

(54) PLASMIDS AND METHODS FOR MONITORING ENDONUCLEASE DIGESTION EFFICIENCY

(75) Inventor: Charles V. Lowry, Albany, NY (US)

(73) Assignee: Albany Medical College, Albany, NY (US)

( * ) Notice: Subject to any disclaimer, the term of this patent is extended or adjusted under 35 U.S.C. 154(b) by 49 days.

(21) Appl. No.: 09/989,534

(22) Filed: Nov. 20, 2001

(65) Prior Publication Data

US 2003/0165847 A1 Sep. 4, 2003

(51) Int. Cl.$^7$ .......................... C12Q 1/68; C12N 15/00
(52) U.S. Cl. .......................... 435/6; 435/4; 435/320.1; 536/23.1; 536/24.2
(58) Field of Search .......................... 435/4, 6, 320.1; 536/23.1, 24.2

(56) References Cited

U.S. PATENT DOCUMENTS

| | | |
|---|---|---|
| 4,237,224 A | 12/1980 | Cohen et al. |
| 4,528,266 A | 7/1985 | Pieczenik |
| 4,657,858 A | 4/1987 | Davison |
| 5,200,333 A | 4/1993 | Wilson |

OTHER PUBLICATIONS

Sikorski et al. A system of shuttle vectors and yeast host strains designed for efficient manipulation of DNA in *Saccharomyces cerevisiae*. Genetics 122: 19–27, May 1989.*

Palmeros et al. A family of removable cassettes designed to obtain antibiotic–resistance–free genomic modifications of *Escherichia coli* and other bacteria. Gene 247: 255–264, Apr. 2000.*

Tsang et al. Biotechniques 22: 68, 1997.*

Fussenegger et al. Biotechnology and Bioengineering 57:1–10, 1998.*

* cited by examiner

*Primary Examiner*—James Ketter
*Assistant Examiner*—David Lambertson
(74) *Attorney, Agent, or Firm*—Heslin Rothenberg Faley & Mesiti P.C.; Kathy Smith Dias, Esq.

(57) ABSTRACT

A method is disclosed herein for monitoring the efficiency of an endonuclease digestion using a plasmid specifically designed for that purpose. The plasmid of the present invention comprises at least two polylinker regions containing a plurality of unique restriction sites distributed so that digestion of the plasmid with any two restriction endonucleases whose sites are represented on the plasmid results in two fragments that are sufficiently different in size from the intact plasmid so as to be readily distinguishable therefrom. To ensure this size differential, the polylinker regions of the plasmid are separated by a spacer segment comprising a restriction site-free nucleic acid sequence that is at least about 15% of the length of the intact plasmid.

34 Claims, 4 Drawing Sheets

SEQUENCE LISTING

```
<160> NUMBER OF SEQ ID NOS: 40

<210> SEQ ID NO 1
<211> LENGTH: 645
<212> TYPE: DNA
<213> ORGANISM: H. sapiens
<220> FEATURE:
<221> NAME/KEY: misc_feature
<222> LOCATION: (1)..(645)
<223> OTHER INFORMATION: restriction site-free nucleotide sequence
      corresponding to nucleotides 72394-73038 of chromosome V

<400> SEQUENCE: 1
```

```
tatataaaaa taataatgtt tttactttttt taagtattgg aagtaccttta gaaatcattg      60 actttgccca actgccccat tttacagttg tggaaaccga ggtcatagaa ttggtaaatt     120
acgaagaaaa ctgtgtttcc tagtaggtct ccctgccttc actctgcctc caccaccagg     180
agtctctgca cccagtcatc tttctaaggg gtgtgccatc catcactccc cacgcaaaac     240
ctctctgtgc cctccaatgc agctagactg aagcctgtga tgtcagtgtg gtcagatccc     300
tgcaacctca gcttgtgttc atggcacact gtgcttctgc tacccctggcc ttctctctgc     360 tgtgtgaaca cactaaggtt taacccttcc cgttgtcttg gaggggaaaa ttctcccaga     420
tattcaggct tctttgtgtc attcagtctc actcagctca aagggcactt cctctgggct     480
gccctaaccc ccaccagaca cccaaactag atgcacaacg ctcgtcactc tttcccatca     540
gcctgattgg atgcctctaa agcatgtacc actatctgta ccactgctca tttattcatt     600
gttcatgttt attgtttgtg tccaatcact gacaggaagc tgcag                     645

<210> SEQ ID NO 2
<211> LENGTH: 553
<212> TYPE: DNA
<213> ORGANISM: H. sapiens
<220> FEATURE:
<221> NAME/KEY: misc_feature
<222> LOCATION: (1)..(553)
<223> OTHER INFORMATION: restriction site-free nucleotide sequence
      corresponding to nucleotides 133197-133749 of chromosome V

<400> SEQUENCE: 2
aagcttttaa gacagaatca tagaccataa aactatttaa taagtacaat gtactaaaaa      60
tatcctttac tgagacagat tggtgaaatt aaaagagcac cagcttaaag atcaggaagc     120
cagatgctgt tctctgctca ggcccagcct caatcatgtg gccctgggca ggcacctcct     180
caacttgacc tcagttttgc cctttttaca atggtatcta taagttcttc ttggctctgc     240
tattctggaa ttatcttatg tagaataagt cttcccaagc tgtgtgggc ttttcctggt     300 agatttgagg gaagttttgt tctgttttgt tttattgttt gcttaccctg ctactgccag     360
tgaagtcaac actacaagca gacagtaagc caggaaacat ttctccctgt caggtcagca     420
catcccatta ggtggatctg gtgctcaagt ttattagatc aggagaccga tgctggggaa     480
ggctcacaga gtggtctgag tcagttgctc taccatgagg ttggagtgta gtagattcaa     540
catcctgtgt aca                                                        553

<210> SEQ ID NO 3
<211> LENGTH: 540
<212> TYPE: DNA
<213> ORGANISM: H. sapiens
<220> FEATURE:
<221> NAME/KEY: misc_feature
<222> LOCATION: (1)..(540)
<223> OTHER INFORMATION: restriction site-free nucleotide sequence
      corresponding to nucleotides 75726-76265 of chromosome V

<400> SEQUENCE: 3
tcatgaggtc aggagattga gaccatcctg gctaacacgg tgaaacccca tctctactaa      60
aaatacaaaa aattagccgg gcgtggtggt gggcacctgt agtcccaact actcgggagg     120
ctgaggcagg agaatggcat gaacctggga ggcagagctt gcagtgagcc tcagattgca     180
ccactgcact ccagcctggg caacagaatg agactccatc tcaaaaaaaa aaaaaacaa     240 cttgtccaag tttatatggc ctggtacagg caggatttag gcaactgaat ccacaggtgc     300
tgctgaacca ccaggagacc tgctgcccaa gtaactgcaa acgggcacc agggactgtc     360
```

```
taggaccaca ggtcgagttc cacctctgcc aacctagttt gttagccctt ccttccttcc    420
ttccttcctt cctccttcct tttctgttct tgcctgccag cttttctctt tctacatttc    480
ttcctcctcc ttccttctct ctgtctcttc tatcctacat taagtataag tttttcatga    540
```

```
<210> SEQ ID NO 4
<211> LENGTH: 536
<212> TYPE: DNA
<213> ORGANISM: H. sapiens
<220> FEATURE:
<221> NAME/KEY: misc_feature
<222> LOCATION: (1)..(536)
<223> OTHER INFORMATION: restriction site-free nucleotide sequence
      corresponding to nucleotides 94154-94684 of chromosome V

<400> SEQUENCE: 4
```

```
ctgcagcagg catctcttgg tgccatgagt cctggtgggc cttattgatt ccttattcat     60
ttcttatcac cccatgtgaa tcagattcag ttgcttcaca ttttcttcac tgctcttatc    120
actgcccgat attatattac agttgtgagt tttgcacctc ttatattaag acagtgtctg    180
ccacatagta agcacttagt atttgctgaa agttgtaaaa gtgcatcaat gagtatccca    240
cagtgccggg cacataatag atattccata aattgttgta aaatagcatt tcctctctgt    300
ccagggaaca gggatgaggg tggtataaat ggggagcatt ttgttcaggg atgttttctg    360
gatgtggcat ttgagctaga ccttaaaaga tggagtacaa ttccacaagg aaggcttagt    420
agttgggcat tccaaacaaa aaggacaggt gtttagacat ggaaagcatt agggacattt    480
gagaaattgg gaatagctca gtttagctgg cagactggaa atacaaagag gaattc        536
```

```
<210> SEQ ID NO 5
<211> LENGTH: 514
<212> TYPE: DNA
<213> ORGANISM: H. sapiens
<220> FEATURE:
<221> NAME/KEY: misc_feature
<222> LOCATION: (1)..(514)
<223> OTHER INFORMATION: restriction site free nucleotide sequence
      corresponding to nucleotides of Chromosome V

<400> SEQUENCE: 5
```

```
agtacttatt acattttagg tcttatttaa ttgtctgtgt tcctctccat tcccaccaac     60
tagggcctga cacataggggg ttcaataatt gtcaagtgat tgacagaatg aatgaatgga   120
tggatgagtg aaaaagtctc tccatttcca gtgtgtattc tctctaatat cttctacatt    180
ctacactgaa attgtctttt tgaaagcctg gacttcttca gtggcttgtc attgccagtg    240
gataaaatgc agacttttca tctgtgcatt caagaactac cacatatagt ctcagcctac    300
catttctctt tttttttttt tttagatgga gcctttctct gctgcccagg ctggagtgca    360
gtggcatggt ctcggttcac tgcaacctct gcctgttggg tgcaagagat tctcctgcct    420
cagcctcctg agtagctggg attacaggca cccaccacca cacccagcta attttttgtat   480 ttttagtaga gatggagttt caccatgttg gcca                                514
```

```
<210> SEQ ID NO 6
<211> LENGTH: 507
<212> TYPE: DNA
<213> ORGANISM: H. sapiens
<220> FEATURE:
<221> NAME/KEY: misc_feature
<222> LOCATION: (1)..(507)
<223> OTHER INFORMATION: restriction site free nucleotide sequence
      corresponding to nucleotides of Chromosome V
```

<400> SEQUENCE: 6

```
gaattcatgt taatccacat agagaattga gagatcagag ccttcaataa atgccaacca      60
acatttacag tgtattgtct gtcagcacag tgctgtgaca gtgctgggga taaaacaaca 1   20 cagacgccag ggcatcagac cctaccccca cggttgcttt atgtactctc agggcacagg    180
gacgctttca ttctgtgctc ttatcacact gacttgtgtc atctcttgac tgtcagtctc    240
tcccactgaa ctacaaacct tttgagagca gaagcccttt ttcttttatt gttttctcag    300
catttcatat cctattgcac aaatcaggac ttggcacata atagatgctc cataagtaat    360
ggttgaataa atgaataaat acatagtacc cgtattagtt tgctagggct tccataacaa    420
aataccacag cctgggtggc ttacacaatg gaattttatt ttctcatggt cttggaggct    480
ggaagtccaa gatcaaggtg cctgcag                                         507
```

<210> SEQ ID NO 7
<211> LENGTH: 488
<212> TYPE: DNA
<213> ORGANISM: H. sapiens
<220> FEATURE:
<221> NAME/KEY: misc_feature
<222> LOCATION: (1)..(488)
<223> OTHER INFORMATION: restriction site free nucleotide sequence
      corresponding to nucleotides of Chromosome V

<400> SEQUENCE: 7

```
aaatttacgc agaagcagga tacagaaagc agccagaagt ggagcagcac cagccggggt      60
ggggaccaag acctcccacc ctccttggtg tctgtctgcc tttgaggtcc ctctgccaaa    120
gtggcgctct gctgagcaaa gtaatccctc agggcactcc aactctgaga cagaatgatt    180
tatagccctg ttaatccacc aggctgtcaa aaacggccac atcagcagac atacacagag    240
acatgcagtc acatacactc aggacaaaaa ataagcccca gaaactgctt gagcaagctc    300
aggcttttct ctagcaccct cctcatttgt tcaagttttt gccatcttta ttttcatttc    360
ctggtttctt ctcacatcct tcctcttttc ccctccaagt tactaaaaat tctaacaatt    420
tctactttta cttctttgtt gttatctgcg gcacatcgtt gccccacccc cactcttggt    480
cgctatag                                                             488
```

<210> SEQ ID NO 8
<211> LENGTH: 477
<212> TYPE: DNA
<213> ORGANISM: H. sapiens
<220> FEATURE:
<221> NAME/KEY: misc_feature
<222> LOCATION: (1)..(477)
<223> OTHER INFORMATION: restriction site free nucleotide sequence
      corresponding to nucleotides of Chromosome V

<400> SEQUENCE: 8

```
ttgcaagctg gagacccaga aaaactgata atgtagtaca agtccaaaca ttggcagact      60
tgagacctgg gaagagccaa tgttttagtt taagtctgtc agtaaaaaga aaccaatgtg    120
ccagctcaaa ggcagacaag catgggaatt ttctattata gggaggaagg tcagccttt     180 tttcctattc aggtcttcaa tggattggac gggaaccatc cacattaggg agggcaatct    240
gctttactta gtctcccaaa tcaaatgtta atctcatcca gaaatatcag cacacacaac    300
cttagaataa tgtctgacca aatgtctggg cacccaatag ctcagtcaag ttgacacata    360
aaattaacca tcacttggcc ggacgctgtg gctcacacct gttatcccag cactttgggt    420
```

```
gggtggatca cctgaggttc cttaggaatg taaagaggtg agcacttaga atctaga        477
```

<210> SEQ ID NO 9
<211> LENGTH: 465
<212> TYPE: DNA
<213> ORGANISM: H. sapiens
<220> FEATURE:
<221> NAME/KEY: misc_feature
<222> LOCATION: (1)..(465)
<223> OTHER INFORMATION: restriction site free nucleotide sequence
      corresponding to nucleotides of Chromosome V

<400> SEQUENCE: 9

```
aagcttacaa cttgctggtg ctgtttcctg ggatttactc cctgctctgg agtatctcta     60
aacctttgga ggtgctacca catgccccac cctcacccca ggttttgatg accaccccat    120
cttttaggag ttcccttat ttttatatcc tcatcctttc tctatccatg ctcagtcatg     180
gtcaatgtga aatctgtgct gtggctttcc tggcttggct cttcatagat aaacctataa    240
agccaagatt tgagaaatct ttctctctct ctctctctct ctctctctct ctctcaataa    300
agttggtgtt cttttttttt tctttagcaa attggcaaca tttcctatca gattatgtat    360
tgttcacagg ctatacaaac tctaggaact atcaggggtt atttggaaga aaacaactg     420
gtgtactatt tttctaaata ctacacctac aaaacatcca atatt                    465
```

<210> SEQ ID NO 10
<211> LENGTH: 26
<212> TYPE: DNA
<213> ORGANISM: Artificial sequence
<220> FEATURE:
<223> OTHER INFORMATION: oligonucleotide used for plasmid construction

<400> SEQUENCE: 10

```
gaattcaaaa gtcgacaaaa ggatcc                                          26
```

<210> SEQ ID NO 11
<211> LENGTH: 26
<212> TYPE: DNA
<213> ORGANISM: Artificial sequence
<220> FEATURE:
<223> OTHER INFORMATION: oligonucleotide used for plasmid construction

<400> SEQUENCE: 11

```
ggatcctttt gtcgactttt gaattc                                          26
```

<210> SEQ ID NO 12
<211> LENGTH: 38
<212> TYPE: DNA
<213> ORGANISM: Artificial sequence
<220> FEATURE:
<223> OTHER INFORMATION: oligonucleotide used for plasmid construction

<400> SEQUENCE: 12

```
gagagaattc tataaagctt cgtattccaa tggggagc                             38
```

<210> SEQ ID NO 13
<211> LENGTH: 34
<212> TYPE: DNA
<213> ORGANISM: Artificial sequence
<220> FEATURE:
<223> OTHER INFORMATION: oligonucleotide used for plasmid construction

<400> SEQUENCE: 13

```
gagagtcgac agaaaacatt ctctagggat tacg                                 34
```

<210> SEQ ID NO 14
<211> LENGTH: 51
<212> TYPE: DNA
<213> ORGANISM: Artificial sequence
<220> FEATURE:
<223> OTHER INFORMATION: oligonucleotide used for plasmid construction

<400> SEQUENCE: 14
gagagtcgac tataagatct ccataccatt gtagtattga ctactaacta c         51

<210> SEQ ID NO 15
<211> LENGTH: 41
<212> TYPE: DNA
<213> ORGANISM: Artificial sequence
<220> FEATURE:
<223> OTHER INFORMATION: oligonucleotide used for plasmid construction

<400> SEQUENCE: 15
gagaggatcc tatactcgag tagaaaacca gattttgcct c                     41

<210> SEQ ID NO 16
<211> LENGTH: 45
<212> TYPE: DNA
<213> ORGANISM: Artificial sequence
<220> FEATURE:
<223> OTHER INFORMATION: oligonucleotide used for plasmid construction

<400> SEQUENCE: 16
agcttaagca tgcggccgcc ggcggtaacc ggtaccacta gttcg                 45

<210> SEQ ID NO 17
<211> LENGTH: 45
<212> TYPE: DNA
<213> ORGANISM: Artificial sequence
<220> FEATURE:
<223> OTHER INFORMATION: oligonucleotide used for plasmid construction

<400> SEQUENCE: 17
aattcgaact agtggtaccg gttaccgccg gcggccgcat gctta                 45

<210> SEQ ID NO 18
<211> LENGTH: 49
<212> TYPE: DNA
<213> ORGANISM: Artificial sequence
<220> FEATURE:
<223> OTHER INFORMATION: oligonucleotide used for plasmid construction

<400> SEQUENCE: 18
gatctgtcta gacgcgtatc gatatcaatt gaggcctgca gctgttaac             49

<210> SEQ ID NO 19
<211> LENGTH: 50
<212> TYPE: DNA
<213> ORGANISM: Artificial sequence
<220> FEATURE:
<223> OTHER INFORMATION: oligonucleotide used for plasmid construction

<400> SEQUENCE: 19
tcgacgttaa cagctgcagg cctcaattga tatcgatacg cgtctagaca            50

<210> SEQ ID NO 20
<211> LENGTH: 42
<212> TYPE: DNA
<213> ORGANISM: Artificial sequence
<220> FEATURE:
<223> OTHER INFORMATION: oligonucleotide used for plasmid construction

```
<400> SEQUENCE: 20
gatcctaggc gccatggcca gctagcccgg gcccatatga gc         42

<210> SEQ ID NO 21
<211> LENGTH: 42
<212> TYPE: DNA
<213> ORGANISM: Artificial sequence
<220> FEATURE:
<223> OTHER INFORMATION: oligonucleotide used for plasmid construction

<400> SEQUENCE: 21
tcgagctcat atgggcccgg gctagctggc catggcgcct ag         42

<210> SEQ ID NO 22
<211> LENGTH: 24
<212> TYPE: DNA
<213> ORGANISM: Artificial sequence
<220> FEATURE:
<223> OTHER INFORMATION: oligonucleotide used for plasmid construction

<400> SEQUENCE: 22
ctagctgcag ctgttaacgt cgac                             24

<210> SEQ ID NO 23
<211> LENGTH: 24
<212> TYPE: DNA
<213> ORGANISM: Artificial sequence
<220> FEATURE:
<223> OTHER INFORMATION: oligonucleotide used for plasmid construction

<400> SEQUENCE: 23
aattgtcgac gttaacagct gcag                             24

<210> SEQ ID NO 24
<211> LENGTH: 13
<212> TYPE: DNA
<213> ORGANISM: Artificial sequence
<220> FEATURE:
<223> OTHER INFORMATION: oligonucleotide used for plasmid construction

<400> SEQUENCE: 24
tatgagctcg aga                                         13

<210> SEQ ID NO 25
<211> LENGTH: 21
<212> TYPE: DNA
<213> ORGANISM: Artificial sequence
<220> FEATURE:
<223> OTHER INFORMATION: oligonucleotide used for plasmid construction

<400> SEQUENCE: 25
tcgatctcga gctcatatgc a                                21

<210> SEQ ID NO 26
<211> LENGTH: 25
<212> TYPE: DNA
<213> ORGANISM: Artificial sequence
<220> FEATURE:
<223> OTHER INFORMATION: oligonucleotide used for plasmid construction

<400> SEQUENCE: 26
ctagcccggg cccactagtt cgaat                            25

<210> SEQ ID NO 27
```

```
<211> LENGTH: 25
<212> TYPE: DNA
<213> ORGANISM: Artificial sequence
<220> FEATURE:
<223> OTHER INFORMATION: oligonucleotide used for plasmid construction

<400> SEQUENCE: 27
tcgaattcga actagtgggc ccggg                                              25

<210> SEQ ID NO 28
<211> LENGTH: 26
<212> TYPE: DNA
<213> ORGANISM: Artificial sequence
<220> FEATURE:
<223> OTHER INFORMATION: oligonucleotide used for plasmid construction

<400> SEQUENCE: 28
agctagatct gtctagacgc gtcatg                                             26

<210> SEQ ID NO 29
<211> LENGTH: 18
<212> TYPE: DNA
<213> ORGANISM: Artificial sequence
<220> FEATURE:
<223> OTHER INFORMATION: oligonucleotide used for plasmid construction

<400> SEQUENCE: 29
acgcgtctag acagatct                                                      18

<210> SEQ ID NO 30
<211> LENGTH: 17
<212> TYPE: DNA
<213> ORGANISM: Artificial sequence
<220> FEATURE:
<223> OTHER INFORMATION: oligonucleotide used for plasmid construction

<400> SEQUENCE: 30
gatcggatcc taggcgc                                                       17

<210> SEQ ID NO 31
<211> LENGTH: 17
<212> TYPE: DNA
<213> ORGANISM: Artificial sequence
<220> FEATURE:
<223> OTHER INFORMATION: oligonucleotide used for plasmid construction

<400> SEQUENCE: 31
cgcggcgcct aggatcc                                                       17

<210> SEQ ID NO 32
<211> LENGTH: 17
<212> TYPE: DNA
<213> ORGANISM: Artificial sequence
<220> FEATURE:
<223> OTHER INFORMATION: oligonucleotide used for plasmid construction

<400> SEQUENCE: 32
gatcaagctt aagcatg                                                       17

<210> SEQ ID NO 33
<211> LENGTH: 15
<212> TYPE: DNA
<213> ORGANISM: Artificial sequence
<220> FEATURE:
<223> OTHER INFORMATION: oligonucleotide used for plasmid construction

<400> SEQUENCE: 33
```

```
cgcatgctta agctt                                                          15

<210> SEQ ID NO 34
<211> LENGTH: 49
<212> TYPE: DNA
<213> ORGANISM: Artificial sequence
<220> FEATURE:
<223> OTHER INFORMATION: oligonucleotide used for plasmid construction

<400> SEQUENCE: 34
agcttaccgg tctagagctc aattggccac ccgggccta ggcctgcag                      49

<210> SEQ ID NO 35
<211> LENGTH: 49
<212> TYPE: DNA
<213> ORGANISM: Artificial sequence
<220> FEATURE:
<223> OTHER INFORMATION: oligonucleotide used for plasmid construction

<400> SEQUENCE: 35
aattctgcag gcctagggcc cgggtggcca attgagctct agaccggta                     49

<210> SEQ ID NO 36
<211> LENGTH: 47
<212> TYPE: DNA
<213> ORGANISM: Artificial sequence
<220> FEATURE:
<223> OTHER INFORMATION: oligonucleotide used for plasmid construction

<400> SEQUENCE: 36
gatcttaagt atcgatgccg gcgccatggt aaccatatgt taactag                       47

<210> SEQ ID NO 37
<211> LENGTH: 47
<212> TYPE: DNA
<213> ORGANISM: Artificial sequence
<220> FEATURE:
<223> OTHER INFORMATION: oligonucleotide used for plasmid construction

<400> SEQUENCE: 37
tcgactagtt aacatatggt taccatggcg ccggcatcga tacttaa                       47

<210> SEQ ID NO 38
<211> LENGTH: 48
<212> TYPE: DNA
<213> ORGANISM: Artificial sequence
<220> FEATURE:
<223> OTHER INFORMATION: oligonucleotide used for plasmid construction

<400> SEQUENCE: 38
tcgagatatc acgcgttcga agctagcggc cgcatgcggt accagctg                      48

<210> SEQ ID NO 39
<211> LENGTH: 48
<212> TYPE: DNA
<213> ORGANISM: Artificial sequence
<220> FEATURE:
<223> OTHER INFORMATION: oligonucleotide used for plasmid construction

<400> SEQUENCE: 39
gatccagctg gtaccgcatg cggccgctag cttcgaacgc gtgatatc                      48

<210> SEQ ID NO 40
<211> LENGTH: 12
<212> TYPE: DNA
```

```
<213> ORGANISM: Artificial sequence
<220> FEATURE:
<223> OTHER INFORMATION: oligonucleotide used for plasmid construction

<400> SEQUENCE: 40
gatcgtcgcg ac                                                          12
```

PLASMIDS AND METHODS FOR MONITORING ENDONUCLEASE DIGESTION EFFICIENCY

FIELD OF THE INVENTION

The invention relates to plasmids, either in circular or linear form, useful in monitoring the efficiency of a restriction endonuclease digestion reaction.

BACKGROUND OF THE INVENTION

Restriction endonucleases are a class of enzymes that occur naturally in bacteria and when they are purified away from other contaminating bacterial components, they can be used in the laboratory to break DNA molecules into precise fragments. They are the biochemical scissors by which genetic engineering and analysis is performed and, therefore, have proved to be indispensable tools in modern genetic research.

Restriction endonucleases act by recognizing and binding to particular sequences of nucleotides (the "recognition sequence") along the DNA molecule. Once bound, they cleave the molecule within, or to one side of, the sequence. Different restriction endonucleases have affinity for different recognition sequences. Close to one hundred different restriction endonucleases have been identified among the many hundreds of baterial species that have been examined to date.

Plasmid construction is an essential technique in the cloning and manipulation of genes. Most plasmid construction strategies are designed to ensure that insertion of a DNA fragment into a vector predominates over the default event in which the vector recircularizes without incorporating an insert. There are four major ways of achieving high insertion ratios. They all rely, in one way or another, on rendering the vector incapable of circularizing without ligating to the insert fragment. For example, use of phosphatased vectors favors a high insertion frequency because dephosphorylated ends can only ligate to phosphorylated ends supplied by the insert. In utilizing this method, however, the phosphatase is difficult to control. TA vectors, used for cloning PCR-amplified DNA, are designed to be linearized in such a way as to leave single 3' thymidine overhangs which can ligate only to adenine over-hangs like those left on the 3' ends of DNA extended by taq (in this method ligation is catalyzed either by DNA ligase or DNA topoisomerase). The TA cloning polymerase method also favors efficient insertion of the PCR product. One limitation of this method is that not all thermostable DNA polymerases used for PCR leave the 3' adenine. Partial fill-in of most 5' restriction site overhangs by Klenow polymerase renders them non-circularizable; an insertable fragment is then generated by partial fill-in of an appropriate restriction site (e.g. a vector cleaved with SalI (G!TCGAC), filled in with T and C can be ligated to Sau3AI (!GATC) fragments filled in with G and A).

The fourth widely used technique is referred to as "forced ligation." This technique makes use of a vector digested with two different restriction enzymes to generate a non-circularizable linear molecule; an insert fragment generated with the same enzymes is ligated in, thereby closing the plasmid. Forced ligation of gel-purifed restriction fragments is the simplest and most efficient method of plasmid construction in situations where segments are transferred from one plasmid to another, or connected together in new combinations, e.g. in mutagenesis, in analysis of gene expression, and in numerous other applications. Double-digested vectors are also convenient for cloning PCR fragments into a construct directly, without the necessity of a TA cloning step, provided that the PCR primers are designed with appropriate restriction sites.

The forced ligation method provides a high percentage of insertion (often greater than 90%), provided that both of the vector sites are fully digested, a criterion which is not always easy to achieve, since many enzymes are of uncertain stability or are inhibited by contaminants present in DNA preparations. Hence demonstration of good digestion is highly desirable before proceeding with the construction; this is also problematic, since complete digestion is impossible to document by agarose electrophoresis when the two sites are in a polylinker; and even when the sites are separated by as much as 10% of the full length of the vector, the desired double cut linear may not be fully resolved from contaminating partially digested molecules. Even a barely detectable residue of partially digested vector leads to an inordinately large number of re-circularized plasmids, requiring a large number of minipreps to be analyzed in search of the desired construct. This is especially troublesome when available insert fragments are present in limited amounts or when lower frequency events, such as triple ligations, are desired.

Because of the uncertainties in obtaining reliable double digests, marker plasmids can be included in mixed test digestions to be sure that both enzymes are active and that neither is inhibited by contaminants in the vector plasmid prep or in a PCR product to be inserted. Suitable marker plasmids can sometimes be found in a plasmid collection for a given pair of enzymes but often none is available, limiting the value of the digest marker maneuver, especially in labs with small plasmid inventories. What is needed is a double digest marker plasmid or set of plasmids which is informative of digestion efficiency for a variety of known restriction endonucleases.

SUMMARY OF THE INVENTION

In one aspect, the invention relates to a plasmid for use in monitoring the efficiency of a restriction endonuclease digestion, comprising at least one spacer segment comprising a nucleic acid sequence that is restriction site-free and at least two polylinker regions containing a plurality of unique restriction sites. The restriction sites are distributed so that digestion of the plasmid with two restriction endonucleases whose sites are represented on the plasmid results in two fragments, each of the fragments being sufficiently different in size from the intact plasmid so as to be readily distinguishable from the plasmid. Generally, fragments that are at least about 15% shorter than the intact plasmid can easily be distinguished from the intact plasmid when visualized on an agarose gel.

In another aspect, the invention relates to a plasmid for monitoring the digestion efficiency of a restriction endonuclease digestion comprising at least one spacer segment comprising a nucleic acid sequence that is restriction site-free and at least two polylinker regions where the polylinker regions contain a plurality of unique restriction sites distributed so that, for any two sites, the two sites are situated within different polylinker regions on at least one plasmid of a set of such plasmids. The polylinker regions are separated by a spacer region of restriction site-free nucleic acid whose length is about 15–85% of the length of the plasmid. Alternatively, the length of the spacer region of restriction site-free nucleic acid may be 20–85%, 30–85%, 40–85% or 50–85% of the length of the intact plasmid. Digestion of the plasmid with two endonucleases whose recognition sites are represented on the plasmid, therefore, results in two fragments, one of the fragments being at least about 15%–85% of the length of the intact plasmid. The plasmid of the present invention further comprises a replication origin and a selectable marker, for example, the amp$^R$ gene. In one embodiment, the plasmid of the present invention comprises a vector backbone of a plasmid such as pUC, pBR322 or pBS.

In a related aspect, the invention relates to a set of plasmids for use in monitoring the efficiency of a restriction endonuclease digestion, wherein each of the plasmids of the set comprises at least one spacer segment comprising a nucleic acid sequence that is restriction site-free and at least two polylinker regions containing a plurality of unique restriction sites distributed so that, for any two sites, the two sites are situated within different polylinker regions on at least one plasmid of the set and the polylinker regions are separated by a spacer segment whose length is about 15–85% of the length of the plasmid.

In yet another aspect, the invention relates to a method for designing a set of plasmids for use in monitoring the efficiency of a restriction endonuclease digestion comprising: (a) identifying at least one spacer segment comprising a nucleic acid sequence that is restriction site-free; (b) identifying a plurality of restriction sites to be represented on the plasmids; (c) assigning each restriction site to a polylinker region on one of the plasmids such that for any two restriction sites there is at least one polylinker in the set that does not contain both sites; (d) distributing the polylinker regions on the plasmids such that the polylinker regions are separated by a spacer segment at least about 15%–85% of the length of the plasmid.

In still another aspect, the invention relates to a method for designing a set of plasmids for monitoring the efficiency of a restriction endonuclease digestion comprising: (a) identifying at least one spacer segment comprising a nucleic acid sequence that is restriction site-free; (b) identifying a plurality of restriction sites to be represented on the plasmids; (c) determining the number of plasmids (b) and the number of polylinker regions (a) on each plasmid necessary to accommodate the desired restriction sites, wherein the maximum number (N) of sites which can be represented is $N=a^b$, where a is the number of polylinkers in each plasmid and b is the number of plasmids in the set; (e) assigning each of the restriction sites to a polylinker region in accordance with a template, wherein the template corresponds to an a×b matrix, and where each site is in a different polylinker from any other site in at least one of the plasmids in the set.

In one aspect, the invention relates to a method of designing a set of three plasmids for monitoring the efficiency of a restriction endonuclease digestion comprising (a) identifying at least two spacer segments comprising a nucleic acid sequence that is restriction site-free; (b) identifying 27 restriction sites to be represented on the three plasmids; (c) numerically ordering the 27 restriction sites; and (d) assigning each of the restriction sites to a polylinker region as follows:
  (i) sites 1–9 are assigned to a first polylinker on a first plasmid, sites 10–18 are assigned to a second polylinker on the first plasmid and sites 19–27 are assigned to a third polylinker on the first plasmid;
  (ii) sites 1, 4, 7, 10, 13, 16, 19, 22 and 25 are assigned to a first polylinker on a second plasmid, sites 2, 5, 8, 11, 14, 17, 20, 23, and 26 are assigned to a second polylinker on the second plasmid and sites 3, 6, 9, 12, 15, 18, 21, 24, and 27 are assigned to a third polylinker on the second plasmid;
  (iii) sites 1, 2, 3, 10, 11, 12, 19, 20 and 21 are assigned to a first polylinker on a third plasmid, sites 4, 5, 6, 13, 14, 15, 22, 23 and 24 are assigned to a second polylinker on the third plasmid and sites 7, 8, 9, 16, 17, 18, 25, 26 and 27 are assigned to a third polylinker on the third plasmid.

The polylinker regions are then distributed on each of the plasmids such that the polylinker regions are separated from each other by a spacer segment at least about 15% of the length of the intact plasmid.

In a related aspect, the invention relates to a set of plasmids designed and constructed according to this method. The plasmids so constructed may further comprise additional restriction sites situated in non-polylinker regions of the plasmids.

In yet another aspect, the invention relates to a method of constructing a set of three plasmids for monitoring the efficiency of a restriction endonuclease digestion comprising:
  (a) identifying at least one spacer segment comprising a nucleic acid sequence that is restriction site-free; (b) identifying 64 restriction sites to be represented on the three plasmids; (c) numerically ordering said restriction sites; and (d) assigning each of said restriction sites to a polylinker region as follows:
    (i) sites 1–16 are assigned to a first polylinker on a first plasmid, sites 17–32 are assigned to a second polylinker on the first plasmid, sites 33–48 are assigned to a third polylinker on the first plasmid and sites 49–64 are assigned to a fourth polylinker on the first plasmid;
    (ii) sites 1–4, 29–32, 41–44 and 53–56 are assigned to a first polylinker on a second plasmid, sites 5–8, 17–20, 45–48 and 57–60 are assigned to a second polylinker on the second plasmid, sites 9–12, 21–24, 33–36 and 61–64 are assigned to a third polylinker on the second plasmid and sites 13–16, 25–28, 37–40 and 49–52 are assigned to a fourth polylinker on the second plasmid;
    (iii) every fourth site beginning with site number 1 is assigned to a first polylinker on a third plasmid, every fourth site beginning with site number 2 is assigned to a second polylinker on the third plasmid, every fourth site beginning with site number 3 is assigned to a third polylinker on the third plasmid; and every fourth site beginning with site number 4 is assigned to a fourth polylinker on the third plasmid. The polylinker regions are then distributed on each of the plasmids such that they are separated by a spacer segment at least about 15% of the length of the plasmid.

In a related aspect, the invention relates to a set of three plasmids constructed according to this method and includes plasmids in which additional restriction sites have been placed in non-polylinker regions of the plasmid.

In yet another aspect, the invention relates to a method for preparing plasmids for monitoring the digestion efficiency of a restriction endonuclease digest reaction, comprising the steps of: (a) transfecting host cells with the monitor plasmid described above; (b) growing the cells under conditions to provide a quantity of cells containing the plasmids; and (c) purifying the plasmids from the cells.

In still another aspect, the invention relates to a method for monitoring the digestion efficiency of a restriction endonuclease digestion reaction comprising: (a) adding a monitor plasmid of the type described above to a sample preparation of a non-monitor plasmid; (b) initiating an endonuclease digestion reaction; (c) allowing the reaction to proceed to completion; and (d) determining, usually by gel electrophoresis of the digested material, whether the monitor plasmid has been digested, wherein digestion of the monitor plasmid indicates digestion of non-monitor plasmids in the sample preparation.

In yet another aspect, the invention relates to a kit for monitoring the digestion efficiency of a restriction endonuclease digestion reaction comprising at least one plasmid where the plasmid contains a plurality of unique restriction sites distributed so that digestion of the plasmid with any two restriction endonucleases represented on the plasmid results in two plasmid fragments, one of the fragments being at least about 15% of the length of the undigested plasmid. The kit may comprise one, two, three, four or more plasmids, as required and includes instructions for use of plasmid(s). The kit may additional include restriction endonucleases whose sites are represented on the plasmid(s) and appropriate buffers.

DETAILED DESCRIPTION OF THE INVENTION

Figure 1:
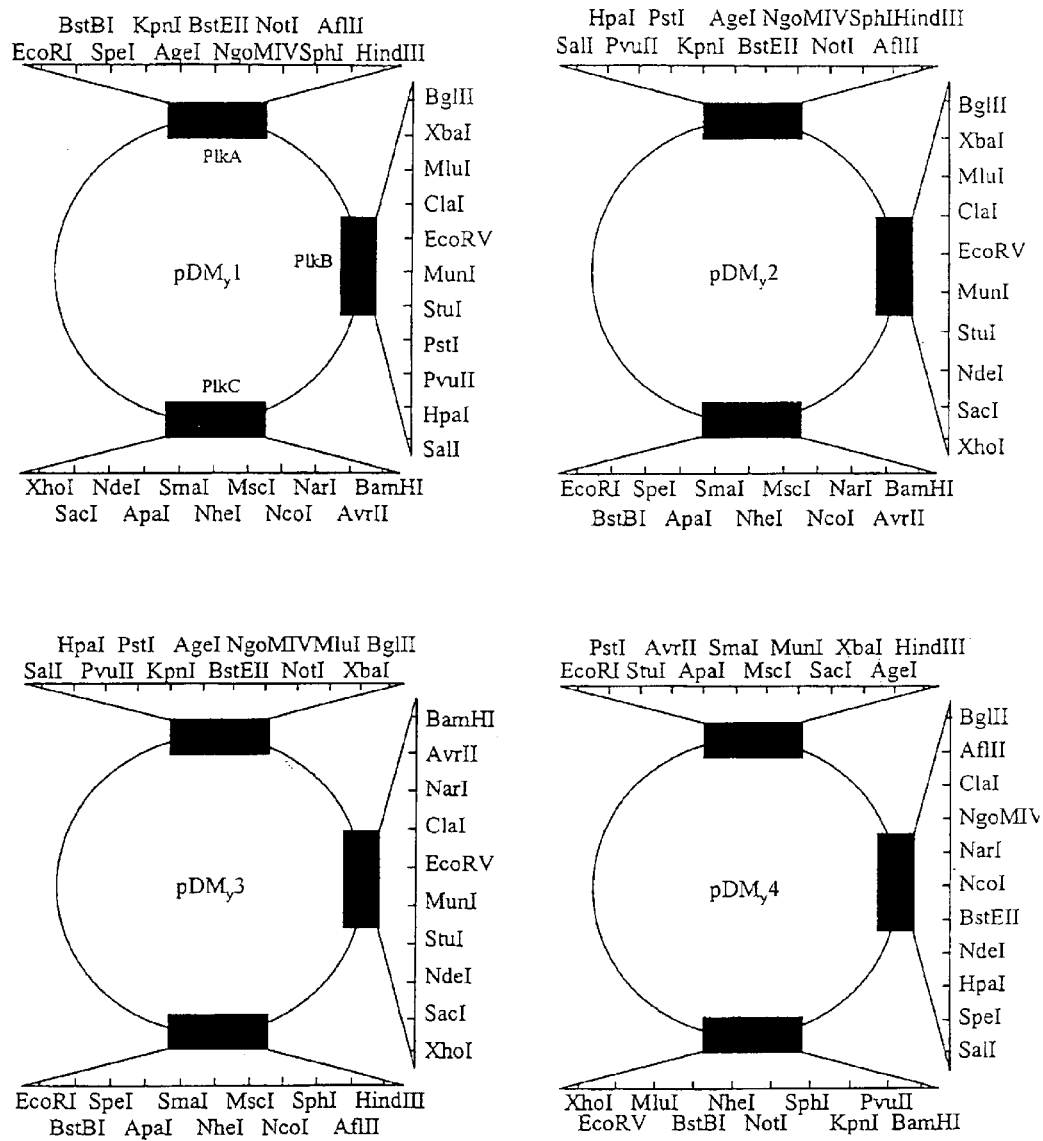
FIG. 1 is a schematic diagram of a set of four plasmids in accordance with one embodiment of the present invention.
Figure 2:
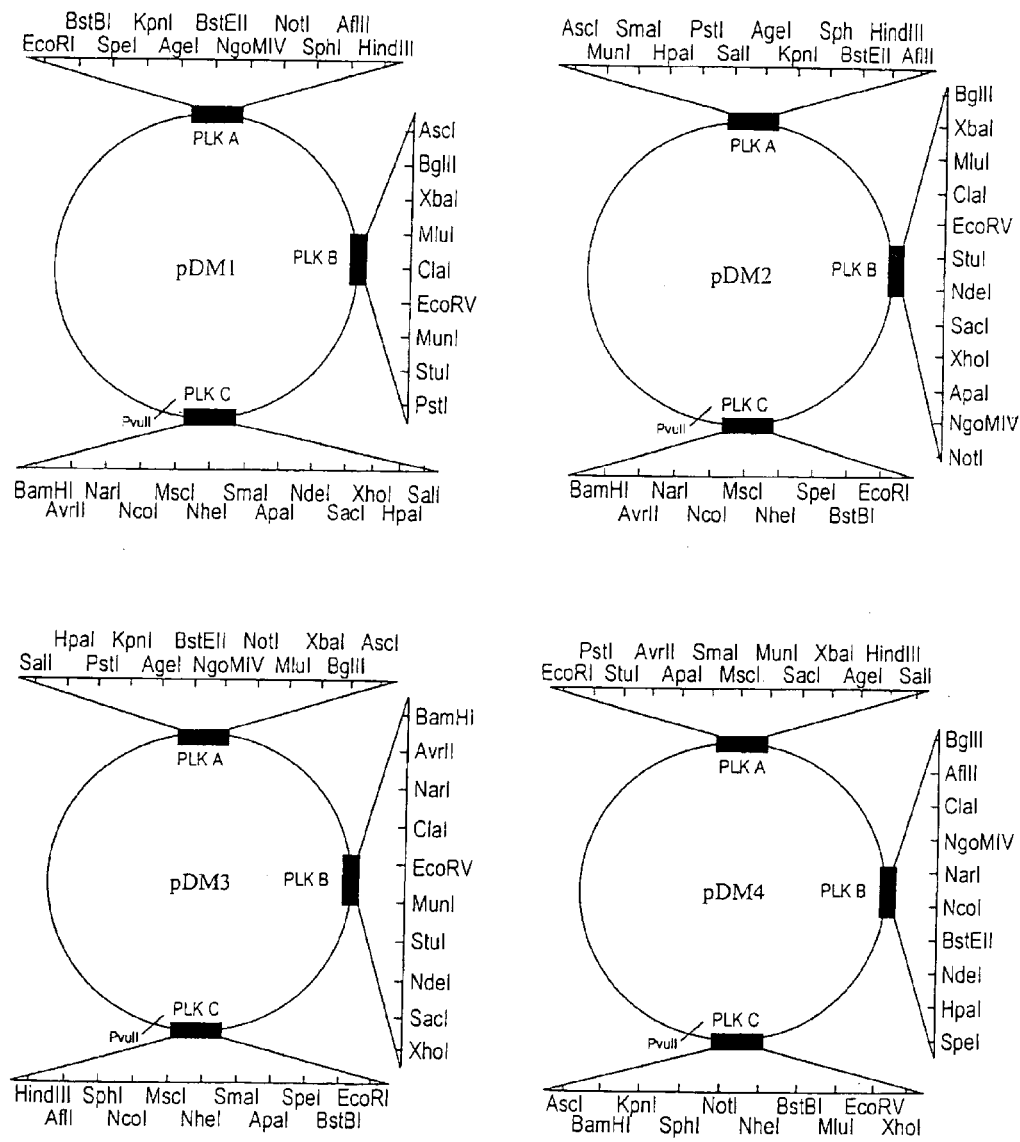
FIG. 2 is a schematic diagram of a set of four plasmids in accordance with another embodiment of the present invention.

In practicing the present invention, many conventional techniques in molecular biology and recombinant DNA technology are used. Such techniques are well known and are explained fully in, for example, Sambrook et al., 2000, *Molecular Cloning: A Laboratory Manual*, Third Edition, Cold Spring Harbor Laboratory Press, Cold Spring Harbor, N.Y.; *Current Protocols in Molecular Biology*, Volumes I, II, and III, 1997 (F. M. Ausubel, ed.).

In the description that follows certain conventions will be followed as regards the usage of terminology:

The term "plasmid" refers to an autonomously replicating, extrachromosomal circular nucleic acid molecule, distinct from the normal host genome and nonessential for cell survival under nonselective conditions. Generally, artificially constructed plasmids are used as cloning vectors. The term, as used herein, refers to a construction of genetic material designed to monitor the efficiency of an restriction endonuclease digestion, in addition to being useful as a cloning vector. Furthermore, the term is meant to encompass intact plasmids in either a circular or linear configuration as well as nucleic acids derived from a plasmid vector. The plasmid may be capable of autonomous replication in a defined host organism such that the plasmid can be reproduced.

The term "intact plasmid" implies that no genetic material has been lost from the plasmid. An "intact plasmid," therefore, is intended to encompass the full-length linear form of the plasmid that is produced by digestion with a single endonuclease, as well as circular plasmids.

The term "restriction site," as it is known in the art, refers to a nucleotide sequence composed typically of 4, 6, or 8 nucleotides that is recognized by a restriction endonuclease.

The term "polylinker" or "polylinker region" refers to a short segment of nucleic acid having several unique restriction endonuclease recognition sites therein. Generally, the polylinker allows the cloning of other nucleic acid sequences into the plasmid backbone.

The term "non-polylinker region," therefore, refers to sections of the plasmid other than the polylinker regions. This term is intended to encompass restriction site-free spacer segments, vector backbone segments and the like.

The term "spacer segment" refers to the restriction site-free segments of DNA between the polylinkers.

The term "vector backbone" refers to a portion of a plasmid derived from a common vector, for example, pUC19. The vector backbone usually comprises an origin of replication and a selectable marker, for example, a gene for antibiotic resistance.

The term "restriction site-free" refers to a segment of nucleic acid in any particular plasmid, that contains none of the restriction endonuclease recognition sites represented in the polylinker regions of that plasmid. This restriction site-free region, therefore, remains intact when exposed to those restriction endonucleases represented in the polylinker regions but not necessarily when exposed to endonucleases not represented in the polylinker regions. The term, as used herein, is not meant to imply that the restriction site-free region is totally devoid of any restriction sites. The restriction site-free region may contain a restriction site for an endonuclease for which the plasmid is not intended to be informative of digestion efficiency.

The term "fully distributed" means that each restriction site to be monitored is separated on the plasmid from each of the other sites to be monitored by a restriction site-free spacer segment at least about 15%–85% of the length of the intact plasmid. In other words, for a plasmid to be informative of double digestion, for any two sites, the two sites must reside in different polylinkers on the plasmid.

Inasmuch as the present invention relates to a specific type of plasmid for monitoring the efficiency of a restriction endonuclease digestion, that is, a "monitor plasmid," the term "non-monitor plasmid" refers to all plasmids other than those encompassed by the present invention.

Plasmid Design

The design of a plasmid or set of plasmids useful for monitoring the efficiency of a restriction endonuclease digestion must take into account the final criterion for an efficient double digestion, that is, the absence of the full-length linear form generated when only one of the enzymes cuts the plasmid. Hence, an important feature of the plasmid(s) of the present invention is that restriction sites for any two endonucleases be situated on the plasmid sufficiently distant from each other to ensure that, following digestion of the plasmid with those two enzymes, the fragments obtained are readily distinguishable from the intact plasmid. This enables any linear plasmid resulting from incomplete digestion to be easily detected. Generally, a fragment whose length is at least about 15% shorter than the length of the intact plasmid can be confidently distinguished from the linearized plasmid on an agarose gel.

In designing a plasmid or plasmid set useful for monitoring the efficiency of digestion by pairs of restriction enzymes, restriction sites are assigned to one of two or more polylinker regions of a plasmid. For each plasmid or plasmid set, there is a limited number of ways of distributing a plurality of restriction sites to achieve full distribution. There is, however, a number of different sets that can be designed according to the criteria defined herein. That is, there is no unique distribution, but the manner of distribution is uniquely defined. A convenient method of distributing the sites for any particular design is by reference to a template specific for each number of polylinkers (a) and plasmids (b). Accordingly, for each number of polylinkers and plasmids there is a different template. Mathematically, the positions in the template correspond to the unique positions in an a×b matrix. Hence all possible fully informative distributions can be represented in terms of the appropriate template.

All possible distributions, therefore, can be represented as a template in which the N positions are numbered according to their distribution in the plasmid set (for example, see Tables 1–9). Toward this end, plasmids are designed according to basic mathematical distributions (for example, a 2×4 matrix for four plasmids each having two polylinkers, a 3×3 matrix for three plasmids each having three polylinkers, a 3×4 matrix for four plasmids each having three polylinkers, a 4×3 matrix for three plasmids each having four polylinkers etc.) so that an optimal number of restriction sites is distributed to polylinker regions of a plasmid or set of plasmids such that for any two restriction sites represented, the two restriction sites reside within different polylinkers on a plasmid separated by a spacer segment.

The polylinkers, preferably three or four per plasmid, are separated from each other by a spacer segment of restriction site-free nucleic acid so that digestion of the resulting plasmid with two restriction endonucleases represented in the polylinkers, generates two fragments, of which the larger is at least about 15% shorter in length than the intact plasmid so that it can be readily distinguished from intact linear plasmid.

Limitations on the size of the polylinker regions are related to practical considerations, for example, practicable plasmid size and the number of polylinkers that will fit while still satisfying the requirement that neighboring polylinkers on the plasmid be separated by a spacer segment at least about 15% of the length of the intact plasmid. The maximum number of sites which can be fully distributed for any given plasmid or set of plasmids is a function of the number of polylinker sites in each plasmid and the number of plasmids. That number, N, is equal to $a^b$ where a is the number of polylinkers per plasmid and b is the total number of plasmids to which the sites are distributed.

It is not necessary, however, that a restriction site be assigned to every position in the template. In some designs it may not be desirable to include the maximum number of restriction sites in the plasmid set In this case the distribution is merely a mathematically "degenerate" form of the full distribution, and more enzyme sites can be added later to unoccupied template positions.

Conversely, it is possible to assign more than one site to the same template position. In the resulting plasmid set, however, it would not be possible to test for digestion by the two corresponding enzymes, but each could still be tested pair-wise with all the other enzymes.

The actual choice of assignment for sites is arbitrary, provided that each site is placed according to the template defined by the a×b matrix for a particular set of plasmids and the sites are fully distributed. Hence, a large number of site distributions are possible for the purpose of monitoring double digestion.

Examples of some of the embodiments intended to be encompassed by the instant invention are provided. The examples given are meant to be illustrative of any possible combination of sites to be represented and in no way is intended to be limited to the particular arrangement of sites shown.

In one embodiment, a set of two plasmids each comprising three polylinker sites would be informative for at least nine different restriction sites; a set of two plasmids each comprising four polylinker sites, as represented by Table 1, illustrates a distribution scheme in which 16 restriction sites can be represented to ensure that, for any two restriction sites represented (i.e., any of the 240 possible combinations), in at least one of the two plasmids, the two restriction sites to be monitored reside within different polylinkers.

In each case, the number of informative sites can be increased slightly by including linked sites and/or by including additional restriction sites in the vector backbone of the plasmid. For example, for the plasmid design shown in Table 1 below, which shows one possible combination of 16 sites to be represented, the inclusion of 6 linked sites, that is recognition sites contained within other recognition sites (template numbers 1, 4, 6–9) increases the number of informative sites to 22. The advantage of this design is that only two plasmids are needed to monitor 478 of the 484 possible combinations of 22 frequently used enzymes. In this design, however, sites that are linked (e.g. EcoRI-MfeI) are both in the same polylinker (Polylinker A) in both plasmids and therefore, cannot be tested for double digestion.

TABLE 1

Two plasmids with four polylinkers: 16 distributed sites plus 6 linked sites

| Plasmid 1 Polylinker | | | | Plasmid 2 Polylinker | | | |
|---|---|---|---|---|---|---|---|
| A | B | C | D | A | B | C | D |
| 1 EcoRI-MfeI | 5 AgeI | 9 SalI-XhoI | 13 HindIII | 1 | 2 | 3 | 4 |
| 2 SacI | 6 BamHI-BglII | 10 MluI | 14 PstI | 5 | 6 | 7 | 8 |
| 3 KpnI | 7 ClaI-BstBI | 11 SacI | 15 NotI(EagI) | 9 | 10 | 11 | 12 |
| 4 SmaI-NruI | 8 XbaI-SpeI | 12 SphI | 16 BspHI | 13 | 14 | 15 | 16 |

A set of three plasmids each having three polylinkers can be informative for 27 (or more) restriction sites. Preliminarily, a list of 27 restriction sites was ordered from 1 to 27, then partitioned into subsets of three sites and assigned to the first, second, and third polylinker positions (see Table 2). For example, for the first plasmid of the set (Plasmid 1), the first three groups, corresponding to the first nine sites, were assigned to the first polylinker position (A), the next three groups of three sites, corresponding to the next nine sites, was assigned to the second polylinker position (B) and the last three groups of three sites, corresponding to the last nine sites, was assigned to the third polylinker position (C).

For the second plasmid (Plasmid 2), the first, fourth, and seventh group of three restriction sites (for example, 1, 2, 3, 10, 11, 12, 19, 20 and 21) are assigned to the first polylinker position (A), the second, fifth, and eighth group of three sites to the second polylinker position (B), and the third, sixth, and ninth group of three sites to the third polylinker position (C). For the third plasmid of the set (Plasmid 3) every third restriction site from the list of 27, starting with site number 1 (i.e. 1,4,7 . . . ), is assigned to the first polylinker position (A), every third site starting with site number 2 (2,5,8 . . . ) to the second polylinker position (B) and every third site starting with site number 3 to the third polylinker position (C). This partitioning of restriction sites among the three plasmids corresponds to a three-by-three matrix, in mathematical terms.

Table 2 provides a template for distribution of 27 sites to a 3 plasmid (three polylinker/plasmid) set.

TABLE 2

Template for 3 plasmids with 3 polylinkers (27 fully distributed sites)

| Plasmid 1 Polylinker site | | | Plasmid 2 Polylinker site | | | Plasmid 3 Polylinker site | | |
|---|---|---|---|---|---|---|---|---|
| A | B | C | A | B | C | A | B | C |
| 1 | 10 | 19 | 1 | 4 | 7 | 1 | 2 | 3 |
| 2 | 11 | 20 | 2 | 5 | 8 | 4 | 5 | 6 |
| 3 | 12 | 21 | 3 | 6 | 9 | 7 | 8 | 9 |
| 4 | 13 | 22 | 10 | 13 | 16 | 10 | 11 | 12 |
| 5 | 14 | 23 | 11 | 14 | 17 | 13 | 14 | 15 |
| 6 | 15 | 24 | 12 | 15 | 18 | 16 | 17 | 18 |
| 7 | 16 | 25 | 19 | 22 | 25 | 19 | 20 | 21 |
| 8 | 17 | 26 | 20 | 23 | 26 | 22 | 23 | 24 |
| 9 | 18 | 27 | 21 | 24 | 27 | 25 | 26 | 27 |

An example of one possible restriction site distribution is shown in Table 3.

TABLE 3

3 plasmids with 3 polylinkers (27 fully distributed sites)

| Polylinker A | template # | Polylinker B | template # | Polylinker C | template # |
|---|---|---|---|---|---|
| pDM1a | | | | | |
| HindIII | 1 | XbaI | 10 | SacI | 19 |
| AflII | 2 | BglII | 11 | NdeI | 20 |
| SphI | 3 | MluI | 12 | XhoI | 21 |
| AgeI | 4 | StuI/MunI | 13 | MscI/ApaI/SmaI | 22 |
| BstEII/NgoMIV | 5 | ClaI | 14 | NcoI | 23 |
| KpnI/NotI | 6 | EcoRV | 15 | NheI | 24 |
| EcoRI | 7 | PstI | 16 | AvrII | 25 |
| SpeI | 8 | SalI/HpaI(HincII) | 17 | NarI | 26 |
| BstBI | 9 | AscI-BssHII | 18 | BamHI | 27 |
| pDM2a | | | | | |
| HindIII | 1 | AgeI | 4 | EcoRI | 7 |
| AflII | 2 | BstEII/NgoMIV | 5 | SpeI | 8 |
| SphI | 3 | KpnI/NotI | 6 | BstBI | 9 |
| XbaI | 10 | StuI/MunI | 13 | PstI | 16 |
| BglII | 11 | ClaI | 14 | SalI/HpaI(HincII) | 17 |
| MluI | 12 | EcoRV | 15 | AscI-BssHII | 18 |
| SacI | 19 | MscI/ApaI/SmaI | 22 | AvrII | 25 |
| NdeI | 20 | NcoI | 23 | NarI | 26 |
| XhoI | 21 | NheI | 24 | BamHI | 27 |
| pDM3a | | | | | |
| HindIII | 1 | AflII | 2 | SphI | 3 |
| AgeI | 4 | BstEII/NgoMIV | 5 | KpnI/NotI | 6 |
| EcoRI | 7 | SpeI | 8 | BstBI | 9 |
| XbaI | 10 | BglII | 11 | MluI | 12 |
| StuI/MunI | 13 | ClaI | 14 | EcoRV | 15 |
| PstI | 16 | SalI/HpaI(HincII) | 17 | AscI-BssHII | 18 |
| SacI | 19 | NdeI | 20 | XhoI | 21 |
| MscI/ApaI/SmaI | 22 | NcoI | 23 | NheI | 24 |
| AvrII | 25 | NarI | 26 | BamHI | 27 |

In another embodiment of the present invention, three plasmids in which the desired restriction sites are distributed among four polylinker regions boosts the number of sites that can be represented to 64 (i.e., $4^3$). In an example of this design option there are four polylinker sites: three located at the ends of two spacer fragments as in the pDM series, and a fourth in the BspHI site between the B-lactamase and ORI regions of the pUC backbone. The advantage of this arrangement is that 64 fully distributed sites can be represented in a set of only three plasmids; for example, this could include the 57 known six-base cutter sites, and the seven six base palindromes interrupted by a single base (e.g. BstEII). For distribution in accordance with this embodiment, the following template would be used:

TABLE 4

Template for 3 plasmids with 4 polylinkers (64 fully distributed sites)

| Plasmid 1 Polylinker | | | | Plasmid 2 Polylinker | | | | Plasmid 3 Polylinker | | | |
|---|---|---|---|---|---|---|---|---|---|---|---|
| A | B | C | D | A | B | C | D | A | B | C | D |
| 1 | 17 | 33 | 49 | 1 | 5 | 9 | 13 | 1 | 2 | 3 | 4 |
| 2 | 18 | 34 | 50 | 2 | 6 | 10 | 14 | 5 | 6 | 7 | 8 |
| 3 | 19 | 35 | 51 | 3 | 7 | 11 | 15 | 9 | 10 | 11 | 12 |
| 4 | 20 | 36 | 52 | 4 | 8 | 12 | 16 | 13 | 14 | 15 | 16 |
| 5 | 21 | 37 | 53 | 29 | 17 | 21 | 25 | 17 | 18 | 19 | 20 |
| 6 | 22 | 38 | 54 | 30 | 18 | 22 | 26 | 21 | 22 | 23 | 24 |
| 7 | 23 | 39 | 55 | 31 | 19 | 23 | 27 | 25 | 26 | 27 | 28 |
| 8 | 24 | 40 | 56 | 32 | 20 | 24 | 28 | 29 | 30 | 31 | 32 |
| 9 | 25 | 41 | 57 | 41 | 45 | 33 | 37 | 33 | 34 | 35 | 36 |
| 10 | 26 | 42 | 58 | 42 | 46 | 34 | 38 | 37 | 38 | 39 | 40 |
| 11 | 27 | 43 | 59 | 43 | 47 | 35 | 39 | 41 | 42 | 43 | 44 |
| 12 | 28 | 44 | 60 | 44 | 48 | 36 | 40 | 45 | 46 | 47 | 48 |
| 13 | 29 | 45 | 61 | 53 | 57 | 61 | 49 | 49 | 50 | 51 | 52 |
| 14 | 30 | 46 | 62 | 54 | 58 | 62 | 50 | 53 | 54 | 55 | 56 |
| 15 | 31 | 47 | 63 | 55 | 59 | 63 | 51 | 57 | 58 | 59 | 60 |
| 16 | 32 | 48 | 64 | 56 | 60 | 64 | 52 | 61 | 62 | 63 | 64 |

In another embodiment of the present invention, a set of four plasmids (referred to herein as pDM1–4) was constructed wherein each plasmid contained three polylinker regions. A four plasmid set containing three polylinkers per plasmid can be used to represent any number of sites up to 81 (i.e., $3^4$). The template for this arrangement is given in Table 5.

TABLE 5

Template for distribution of 81 sites

| pDM1 Polylinker | | | pDM2 Polylinker | | | pDM3 Polylinker | | | pDM4 Polylinker | | |
|---|---|---|---|---|---|---|---|---|---|---|---|
| A | B | C | A | B | C | A | B | C | A | B | C |
| 1 | 28 | 55 | 1 | 10 | 19 | 1 | 4 | 7 | 1 | 2 | 3 |
| 2 | 29 | 56 | 2 | 11 | 20 | 2 | 5 | 8 | 4 | 5 | 6 |
| 3 | 30 | 57 | 3 | 12 | 21 | 3 | 6 | 9 | 7 | 8 | 9 |
| 4 | 31 | 58 | 4 | 13 | 22 | 10 | 13 | 16 | 10 | 11 | 12 |
| 5 | 32 | 59 | 5 | 14 | 23 | 11 | 14 | 17 | 13 | 14 | 15 |
| 6 | 33 | 60 | 6 | 15 | 24 | 12 | 15 | 18 | 16 | 17 | 18 |
| 7 | 34 | 61 | 7 | 16 | 25 | 19 | 22 | 25 | 19 | 20 | 21 |
| 8 | 35 | 62 | 8 | 17 | 26 | 20 | 23 | 26 | 22 | 23 | 24 |
| 9 | 36 | 63 | 9 | 18 | 27 | 21 | 24 | 27 | 25 | 26 | 27 |
| 10 | 37 | 64 | 28 | 37 | 46 | 28 | 31 | 34 | 28 | 29 | 30 |
| 11 | 38 | 65 | 29 | 38 | 47 | 29 | 32 | 35 | 31 | 32 | 33 |
| 12 | 39 | 66 | 30 | 39 | 48 | 30 | 33 | 36 | 34 | 35 | 36 |
| 13 | 40 | 67 | 31 | 40 | 49 | 37 | 40 | 43 | 37 | 38 | 39 |
| 14 | 41 | 68 | 32 | 41 | 50 | 38 | 41 | 44 | 40 | 41 | 42 |
| 15 | 42 | 69 | 33 | 42 | 51 | 39 | 42 | 45 | 43 | 44 | 45 |
| 16 | 43 | 70 | 34 | 43 | 52 | 46 | 49 | 52 | 46 | 47 | 48 |
| 17 | 44 | 71 | 35 | 44 | 53 | 47 | 50 | 53 | 49 | 50 | 51 |
| 18 | 45 | 72 | 36 | 45 | 54 | 48 | 51 | 54 | 52 | 53 | 54 |
| 19 | 46 | 73 | 55 | 64 | 73 | 55 | 58 | 61 | 55 | 56 | 57 |
| 20 | 47 | 74 | 56 | 65 | 74 | 56 | 59 | 62 | 58 | 59 | 60 |
| 21 | 48 | 75 | 57 | 66 | 75 | 57 | 60 | 63 | 61 | 62 | 63 |
| 22 | 49 | 76 | 58 | 67 | 76 | 64 | 67 | 70 | 64 | 65 | 66 |
| 23 | 50 | 77 | 59 | 68 | 77 | 65 | 68 | 71 | 67 | 68 | 69 |
| 24 | 51 | 78 | 60 | 69 | 78 | 66 | 69 | 72 | 70 | 71 | 72 |
| 25 | 52 | 79 | 61 | 70 | 79 | 73 | 76 | 79 | 73 | 74 | 75 |
| 26 | 53 | 80 | 62 | 71 | 80 | 74 | 77 | 80 | 76 | 77 | 78 |
| 27 | 54 | 81 | 63 | 72 | 81 | 75 | 78 | 81 | 79 | 80 | 81 |

As discussed above, less than the maximum number of sites can be distributed in any template. One example, as shown in Table 6, is a distribution of 33 sites to a template suitable for possible distribution of 81 sites, i.e., a four plasmid set, where each plasmid has three polylinkers. This is the pDM1–4 set, a variation of the $pDM_u1$–4a set shown in Table 8. The template position number (template #) for each site is shown next to the enzyme name.

TABLE 6 pDM1-4 Series (33 polylinker sites)

| Polylinker A | | Polylinker B | | Polylinker C | |
|---|---|---|---|---|---|
| | template # | | template # | | template # |
| | | pDM1 | | | |
| AgeI | 1 | PstI | 28 | SalI(HincII) | 55 |
| BstEII | 2 | AscI(BssHII) | 30 | HpaI(HincII) | 56 |
| KpnI | 3 | MunI | 31 | SmaI | 61 |
| HindIII | 7 | XbaI | 37 | SacI | 67 |
| AflII | 8 | BglII | 38 | NdeI | 68 |
| SphI | 9 | MluI | 39 | XhoI | 69 |
| NgoMIV | 11 | StuI | 40 | ApaI | 70 |
| NotI | 12 | ClaI | 41 | AvrII | 76 |
| EcoRI | 25 | EcoRV | 42 | NarI | 77 |
| SpeI | 26 | | | BamHI | 78 |

TABLE 6-continued pDM1-4 Series (33 polylinker sites)

| Polylinker A | template # | Polylinker B | template # | Polylinker C | template # |
|---|---|---|---|---|---|
| BstBI | 27 | | | MscI | 79 |
| | | | | NcoI | 80 |
| | | | | NheI | 81 | pDM2

| Polylinker A | template # | Polylinker B | template # | Polylinker C | template # |
|---|---|---|---|---|---|
| AgeI | 1 | XbaI | 37 | EcoRI | 25 |
| BstEII | 2 | BglII | 38 | SpeI | 26 |
| KpnI | 3 | MluI | 39 | BstBI | 27 |
| HindIII | 7 | StuI | 40 | AvrII | 76 |
| AflII | 8 | ClaI | 41 | NarI | 77 |
| SphI | 9 | EcoRV | 42 | BamHI | 78 |
| PstI | 28 | SacI | 67 | MscI | 79 |
| AscI(BssHII) | 30 | NdeI | 68 | NcoI | 80 |
| MunI | 31 | XhoI | 69 | NheI | 81 |
| SalI (HincII) | 55 | ApaI | 70 | | |
| HpaI(HincII) | 56 | NgoMIV | 11 | | |
| SmaI | 61 | NotI | 12 | | | pDM3

| Polylinker A | template # | Polylinker B | template # | Polylinker C | template # |
|---|---|---|---|---|---|
| AgeI | 1 | MunI | 31 | HindIII | 7 |
| BstEII | 2 | StuI | 40 | AflII | 8 |
| kpnI | 3 | ClaI | 41 | SphI | 9 |
| NgoMIV | 11 | EcoRV | 42 | EcoRI | 25 |
| NotI | 12 | SacI | 67 | SpeI | 26 |
| PstI | 28 | NdeI | 68 | BstBI | 27 |
| AscI(BssHII) | 30 | XhoI | 69 | SmaI | 61 |
| XbaI | 37 | AvrII | 76 | ApaI | 70 |
| BglII | 38 | NarI | 77 | MscI | 79 |
| MluI | 39 | BamHI | 78 | NcoI | 80 |
| SalI(HincII) | 55 | | | NheI | 81 |
| HpaI(HincII) | 56 | | | | | pDM4

| Polylinker A | template # | Polylinker B | template # | Polylinker C | template # |
|---|---|---|---|---|---|
| AgeI | 1 | BstEII | 2 | KpnI | 3 |
| HindIII | 7 | AflII | 8 | SphI | 9 |
| EcoRI | 25 | NgoMIV | 11 | NotI | 12 |
| PstI | 28 | SpeI | 26 | BstBI | 27 |
| MunI | 31 | BglII | 38 | AscI-BssHII | 30 |
| XbaI | 37 | ClaI | 41 | EcoRV | 42 |
| StuI | 40 | HpaI(HincII) | 56 | MluI | 39 |
| SalI(HincI) | 55 | NdeI | 68 | XhoI | 69 |
| SmaI | 61 | NarI | 77 | BamHI | 78 |
| SacI | 67 | NcoI | 80 | NheI | 81 |
| ApaI | 70 | | | | |
| AvrII | 76 | | | | |
| MscI | 79 | | | | |

Expansion of pDM1–4 plasmid set to include 81 sites

The arrangement illustrated in Table 6, above, is actually informative for 43 sites. Thirty-three (33) sites are fully distributed within the polylinker regions of the plasmids and "informative" for monitoring double digestions. Polylinker sites are listed according to their template number, rather than in other order they are arranged in the polylinker. Additionally, there are 3 sites located in the vector backbone (BspHI, PvuI and FspI) that are fully informative and 7 other sites (ScaI, PvuII, AcII, PciI, ApaLI, AseI and DraI) in the vector backbone that are informative for nearly all combinations. HincII sites within SalI and HpaI are informative in this arrangement.

The pDM series shown above in Table 6 can be expanded in three stages to include up to 81 (=3⁴) fully distributed sites. One possible version including all six-base palindromes and several other commonly used sites is shown in Table 8. Distribution of sites to the 81 available positions would be in accordance with the template shown in Table 5. Construction of pDM1–4 is described in detail below. Expansion of the pDM1–4 plasmid set could be accomplished as follows:

(1) Insert new sites in polylinkers of pDM1–4. The thirty-three (33) positions already occupied in the template in the pDM1–4 set are shown in Table 7. New sites to be inserted are assigned to one of the remaining 48 positions of the 81 possible in the pDM template (see Table 7). For example, the ApoI site is assigned #4 and included in polylinker A of pDM1, A of pDM2, B of pDM3, and A of pDM4, as dictated by the template. PmlI is assigned #5 and placed in polylinkers A, A, B, and B, respectively; etc.

TABLE 7

Template for distribution of 81 sites pDM$_U$1-4

| | pDM$_U$1 Polylinker | | | pDM$_U$2 Polylinker | | | pDM$_U$3 Polylinker | | | pDM$_U$4 Polylinker | | |
|---|---|---|---|---|---|---|---|---|---|---|---|---|
| | A | B | C | A | B | C | A | B | C | A | B | C |
| | 1 AgeI | 28 PstI | 55 SalI | 1 | 10 | 19 | 1 | 4 | 7 | 1 | 2 | 3 |
| | 2 BstEII | 29 | 56 HpaI | 2 | 11 | 20 | 2 | 5 | 8 | 4 | 5 | 6 |
| | 3 KpnI | 30 AscI | 57 | 3 | 12 | 21 | 3 | 6 | 9 | 7 | 8 | 9 |
| | 4 | 31 MunI | 58 | 4 | 13 | 22 | 10 | 13 | 16 | 10 | 11 | 12 |
| | 5 | 32 | 59 | 5 | 14 | 23 | 11 | 14 | 17 | 13 | 14 | 15 |
| | 6 | 33 | 60 | 6 | 15 | 24 | 12 | 15 | 18 | 16 | 17 | 18 |
| | 7 HindIII | 34 | 61 SmaI | 7 | 16 | 25 | 19 | 22 | 25 | 19 | 20 | 21 |
| | 8 AflII | 35 | 62 | 8 | 17 | 26 | 20 | 23 | 26 | 22 | 23 | 24 |
| | 9 SphI | 36 | 63 | 9 | 18 | 27 | 21 | 24 | 27 | 25 | 26 | 27 |
| | 10 | 37 XbaI | 64 | 28 | 37 | 46 | 28 | 31 | 34 | 28 | 29 | 30 |
| | 11 NgoMIV | 38 BglII | 65 | 29 | 38 | 47 | 29 | 32 | 35 | 31 | 32 | 33 |
| | 12 NotI | 39 MluI | 66 | 30 | 39 | 48 | 30 | 33 | 36 | 34 | 35 | 36 |
| | 13 | 40 StuI | 67 SacI | 31 | 40 | 49 | 37 | 40 | 43 | 37 | 38 | 39 |
| | 14 | 41 ClaI | 68 NdeI | 32 | 41 | 50 | 38 | 41 | 44 | 40 | 41 | 42 |
| | 15 | 42 EcoRV | 69 XhoI | 33 | 42 | 51 | 39 | 42 | 45 | 43 | 44 | 45 |
| | 16 | 43 | 70 ApaI | 34 | 43 | 52 | 46 | 49 | 52 | 46 | 47 | 48 |
| | 17 | 44 | 71 | 35 | 44 | 53 | 47 | 50 | 53 | 49 | 50 | 51 |
| | 18 | 45 | 72 | 36 | 45 | 54 | 48 | 51 | 54 | 52 | 53 | 54 |
| | 19 | 46 | 73 | 55 | 64 | 73 | 55 | 58 | 61 | 55 | 56 | 57 |
| | 20 | 47 | 74 | 56 | 65 | 74 | 56 | 59 | 62 | 58 | 59 | 60 |
| | 21 | 48 | 75 | 57 | 66 | 75 | 57 | 60 | 63 | 61 | 62 | 63 |
| | 22 | 49 | 76 AvrII | 58 | 67 | 76 | 64 | 67 | 70 | 64 | 65 | 66 |
| | 23 | 50 | 77 NarI | 59 | 68 | 77 | 65 | 68 | 71 | 67 | 68 | 69 |
| | 24 | 51 | 78 BamHI | 60 | 69 | 78 | 66 | 69 | 72 | 70 | 71 | 72 |
| | 25 EcoRI | 52 | 79 MscI | 61 | 70 | 79 | 73 | 76 | 79 | 73 | 74 | 75 |
| | 26 SpeI | 53 | 80 NcoI | 62 | 71 | 80 | 74 | 77 | 80 | 76 | 77 | 78 |
| | 27 BstBI | 54 | 81 NheI | 63 | 72 | 81 | 75 | 78 | 81 | 79 | 80 | 81 |

For construction of the plasmids, 12 oligonucleotides containing the new sites are synthesized and ligated into the 12 polylinker sites of the pDM1–4 plasmids using methods well known to those of skill in the art.

(2) Install new restriction site-free fragments. To make all the polylinker sites unique, the two restriction site-free segments in pDM1–4 would be replaced with fragments (as described above) generated by PCR from segments of genomic DNA lacking the new sites of interest.

(3) Eliminate redundant sites from vector backbone. Some sites which would normally appear in the pUC vector but which are now included in the new polylinker regions are eliminated, using various standard methods well known to those of skill in the art.

TABLE 8 pDM$_U$1-4 Expanded 4-plasmid set with 72 sites (and 9 open positions)

| pDM$_U$ 1 Polylinker | | | pDM$_U$ 2 | | | pDM$_U$ 3 | | | pDM$_U$ 4 | | |
|---|---|---|---|---|---|---|---|---|---|---|---|
| A | B | C | A | B | C | A | B | C | A | B | C |
| 1 AgeI | 28 PstI-SbfI__ | 55 SalI-HincII | 1 | 10 | 19 | 1 | 4 | 7 | 1 | 2 | 3 |
| 2 BstEII‡ | 29 BssHII-AscI | 56 HpaI-HincII | 2 | 11 | 20 | 2 | 5 | 8 | 4 | 5 | 6 |
| 3 KpnI | 30 AscI__ | 57 | 3 | 12 | 21 | 3 | 6 | 9 | 7 | 8 | 9 |
| 4 ApoI | 31 MunI | 58 ApaLI* | 4 | 13 | 22 | 10 | 13 | 16 | 10 | 11 | 12 |
| 5 [taatta]§ | 32 NruI | 59 [ttgcaa] | 5 | 14 | 23 | 11 | 14 | 17 | 13 | 14 | 15 |
| 6 AclI* | 33 PvuI*-SgfI | 60 AseI* | 6 | 15 | 24 | 12 | 15 | 18 | 16 | 17 | 18 |
| 7 HindIII | 34 BclI | 61 SmaI-SrfI | 7 | 16 | 25 | 19 | 22 | 25 | 19 | 20 | 21 |
| 8 AflII | 35 AfeI | 62 BlpI | 8 | 17 | 26 | 20 | 23 | 26 | 22 | 23 | 24 |
| 9 SphI | 36 [cgcgcg] | 63 Bsu36I | 9 | 18 | 27 | 21 | 24 | 27 | 25 | 26 | 27 |
| 10 PmlI | 37 XbaI | 64 RsrII | 28 | 37 | 46 | 28 | 31 | 34 | 28 | 29 | 30 |
| 11 NaeI-FseI† | 38 BglII | 65 SexAI | 29 | 38 | 47 | 29 | 32 | 35 | 31 | 32 | 33 |
| 12 EagI-NotI | 39 MluI | 66 Sse8647I | 30 | 39 | 48 | 30 | 33 | 36 | 34 | 35 | 36 |
| 13 AatII | 40 StuI | 67 SacI | 31 | 40 | 49 | 37 | 40 | 43 | 37 | 38 | 39 |
| 14 SnaBI | 41 ClaI | 68 NdeI | 32 | 41 | 50 | 38 | 41 | 44 | 40 | 41 | 42 |
| 15 PvuII* | 42 EcoRV | 69 XhoI | 33 | 42 | 51 | 39 | 42 | 45 | 43 | 44 | 45 |
| 16 [tagcta] | 32 FspI* | 70 ApaI | 34 | 43 | 52 | 46 | 49 | 52 | 46 | 47 | 48 |
| 17 SspI | 33 ScaI* | 71 SanDI | 35 | 44 | 53 | 47 | 50 | 53 | 49 | 50 | 51 |
| 18 PciI* | 34 BsiWI | 72 | 36 | 45 | 54 | 48 | 51 | 54 | 52 | 53 | 54 |
| 19 BspHI* | 35 BsrGI | 73 PmeI-DraI* | 55 | 64 | 73 | 55 | 58 | 61 | 55 | 56 | 57 |
| 20 BspEI | 36 [atatat] | 74 SwaI-DraI* | 56 | 65 | 74 | 56 | 59 | 62 | 58 | 59 | 60 |
| 21 SacII | 43 [ctatag] | 75 | 57 | 66 | 75 | 57 | 60 | 63 | 61 | 62 | 63 |
| 22 | 44 BstZ17I | 76 AvrII | 58 | 67 | 76 | 64 | 67 | 70 | 64 | 65 | 66 |

TABLE 8-continued pDM_II 1-4 Expanded 4-plasmid set with 72 sites (and 9 open positions)

| pDM_U 1 Polylinker | | | pDM_II 2 | | | pDM_II 3 | | | pDM_II 4 | | |
|---|---|---|---|---|---|---|---|---|---|---|---|
| A | B | C | A | B | C | A | B | C | A | B | C |
| 23 | 45 PsiI | 77 NarI | 59 | 68 | 77 | 65 | 68 | 71 | 67 | 68 | 69 |
| 24 | 46 NsiI | 78 BamHI | 60 | 69 | 78 | 66 | 69 | 72 | 70 | 71 | 72 |
| 25 EcoRI | 52 | 79 MscI | 61 | 70 | 79 | 73 | 76 | 79 | 73 | 74 | 75 |
| 26 SpeI | 53 | 80 NcoI | 62 | 71 | 80 | 74 | 77 | 80 | 76 | 77 | 78 |
| | | | | | | | | | | | 81 |

Sites with asterisks are ordinarily present in the vector backbone and would need to be removed to be fully informative.
§Bracketed sequences indicate six base palindromes for still undiscovered enzymes.
†Double sites represent eight-base cutter sites with internal six-base cutter sites: applies to FseI, NotI, SbfI, AscI, SgfI, PmeI, SwaI, and SrfI.
‡BstEII, BlpI, Bsu36I, RsrII, SexAI, Sse8647I, and SanDI are palindromes interrupted by a single nucleotide.

DraI, contained within both SwaI and PmeI is fully distributed in this arrangement. In the same way, so are the HincII sites, which are isoschizomeric with SalI and HpaI.

Another example of a distribution of less than the maximum number of sites is give in Table 9.

Figure 4:
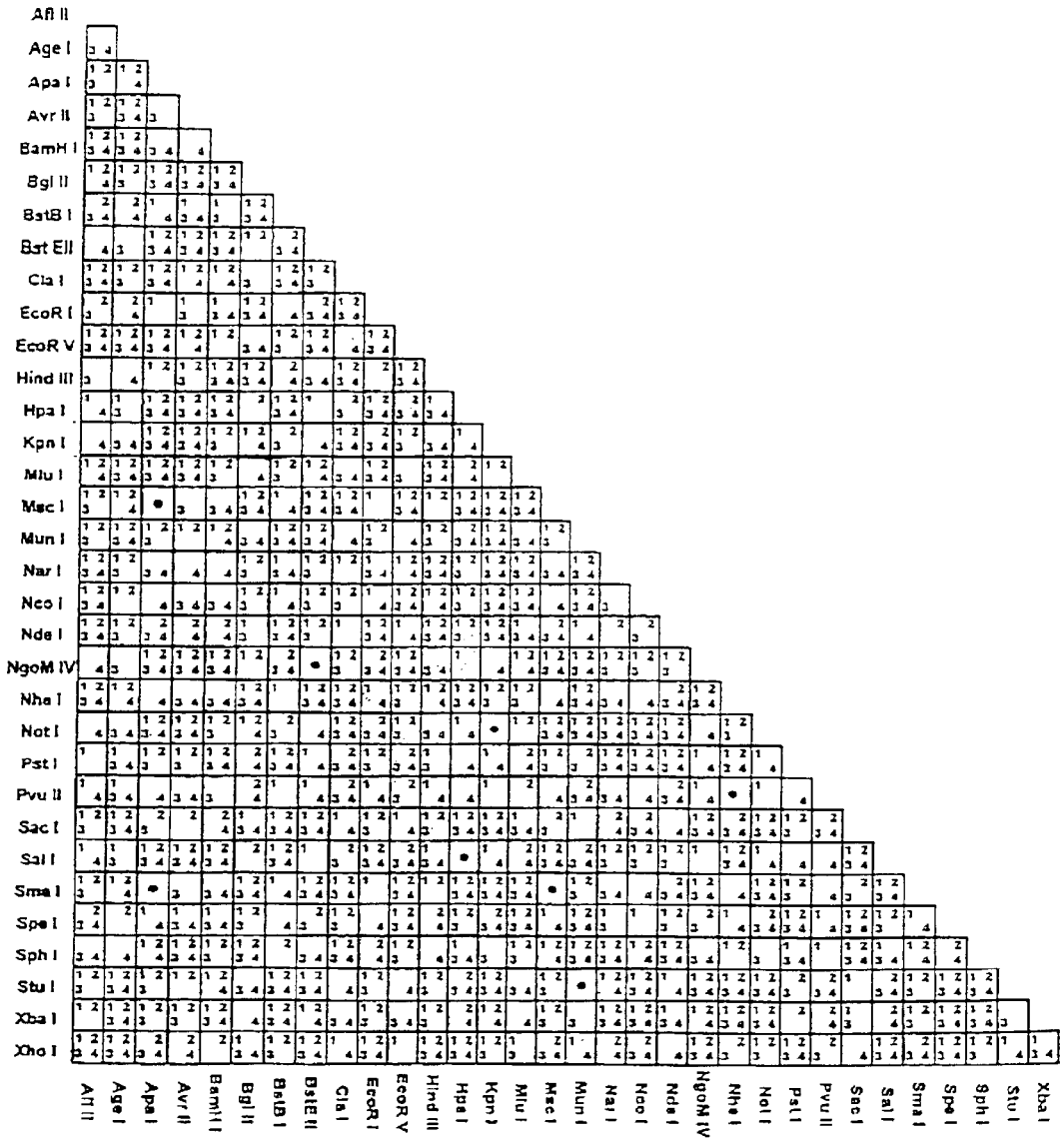
FIG. 4 is an example of a chart to be included with instructions for use of digestion monitor plasmids indicating the appropriate plasmid of a set of plasmids to be used to monitor the digestion efficiency of any two endonucleases represented on the plasmids.

TABLE 9 pDM_y plasmid set (see FIG. 1 and 4)

| Polylinker A | Polylinker B | Polylinker C |
|---|---|---|
| pDM_y1 | | |
| Hind III | Bgl II | Xho I |
| Afl II | Xba I | Sac I |
| Sph I | Mlu I | Nde I |
| Not I | Cla I | Apa I |
| NgoM IV | EcoR V | Sma I |
| BstE II | Mun I | Nhe I |
| Age I | Stu I | Msc I |
| Kpn I | Pst I | Nco I |
| Spe I | Hpa I | Nar I |
| BstB I | Sal I | Avr II |
| EcoR I | | BamH I |
| pDM_y2 | | |
| Hind III | Bgl II | EcoR I |
| Afl II | Xba I | BstB I |
| Sph I | Mlu I | Spe I |
| Not I | Cla I | Apa I |
| NgoM IV | EcoR V | Sma I |
| BstE II | Mun I | Nhe I |
| Age I | Stu I | Msc I |
| Kpn I | Nde I | Nco I |
| Pst I | Sac I | Nar I |
| Hpa I | Xho I | Avr II |
| Sal I | | BamH I |
| pDM_y3 | | |
| Bgl II | BamH I | EcoR I |
| Xba I | Avr II | BstB I |
| Mlu I | Nar I | Spe I |
| Not I | Cla I | Apa I |
| NgoM IV | EcoR V | Sma I |
| BstE II | Mun I | Nhe I |
| Age I | Stu I | Msc I |
| Kpn I | Nde I | Nco I |
| Pst I | Sac I | Sph I |
| Hpa I | Xho I | Afl II |
| Sal I | | Hind III |
| pDM_y4 | | |
| Hind III | Bgl II | Xho I |
| Age I | Afl II | EcoR V |

TABLE 9-continued pDM_y plasmid set (see FIG. 1 and 4)

| Polylinker A | Polylinker B | Polylinker C |
|---|---|---|
| Xba I | Cla I | Mlu I |
| Sac I | NgoM IV | Bst BI |
| Mun I | Nar I | Nhe I |
| Msc I | Nco I | Not I |
| Sma I | Bst EII | Sph I |
| Apa I | Nde I | Kpn I |
| Avr II | Hpa I | BamH I |
| Stu I | Spe I | |
| Pst I | Sal I | |
| EcoR I | | |

In this embodiment, sites are distributed in three polylinkers in each of four plasmids, as shown in FIG. 1. In this plasmid set, some sites are "linked," that is, they are present in the same polylinker in all four plasmids (e.g. SalI and HpaI, or NgoM IV and BstEII.) Hence, these plasmids can't be used for testing digestion of those two pairs of enzymes. A summary of which plasmids in the set can be used for any given pair of sites is tabulated in FIG. 4; a dot represents linked sites.

Construction of Plasmids

Suitable Vectors

Due to the relatively high copy number of plasmids produced, plasmids of the pUC series and pUC-based plasmids, such as the pBLUESCRIPT® series are most preferred as vectors for the construction of the digestion monitor plasmids of the present invention. Other suitable plasmids, however, include, without limitation, other plasmids of bacterial origin, for example pBR322.

Vector Backbone

A commonly used plasmid is selected to provide the vector backbone that contains the genetic elements needed for replication of the plasmid in host cells and for genetic selection in transformed cells. The vector backbone is kept as short as possible, and should not contain sites that are contained in the polylinkers of the digestive monitor, though these can usually be removed, if necessary, without affecting vector functions. A convenient starting vector is pUC19, although other vectors are equivalent for purposes of constructing digestion monitors. The segment between nucleotides # 474 and # 2501 of pUC19 is used for all the constructions described herein, with the polylinker and spacer segments assembled and inserted between these points.

Construction of Polylinkers

Polylinkers are constructed, using techniques well known to the skilled artisan, by annealing together synthetic oligonucleotides comprising the desired recognition sites. These polylinker regions are then ligated into the vector backbone using techniques well known to those of skill in the art.

Construction of Spacer Segments

Spacer segments are generated by PCR amplification of restriction site-free DNA sequences, for example, sequences obtained from the published genome of S. cerevisiae or H. sapiens. During the amplification, restriction sites are added to the ends of the fragments so that they can be ligated into the vector backbone. The spacer segments are at least about 15% of the length of the completed plasmid, and are used to separate the polylinker regions of the plasmid. A plasmid that is around 4 kb will, therefore, contain restriction site-free regions at least about 600 bp in length.

Where more than one spacer segment is required for the construction of a plasmid, preferably, the nucleotide sequence of the spacer segments are different, to avoid recombination and deletion events between the spacer segment sequences.

Identification of Restriction Site-free Segments

In one embodiment of the present invention, as exemplified by the pDM1–4 and pDm1–4 and pDm$_y$1–4 sets (Tables 6 and 9, respectively)the restriction site-free spacer DNA segments chosen for insertion between the three polylinker sites were an 891 bp and a 1020 bp segment located on Chromosome V of S. cerevisiae at nucleotide numbers (NT#) 104477–105368 and 108958–109978, respectively. These were identified by testing a selection of segments chosen at random from the S. cerevisiae sequence database, using DNasis software to locate restriction sites. For larger numbers of restriction sites a more systematic method is needed to identify restriction site-free segments. For example, to obtain spacer segments for the 72 site-pDM$_u$1–4 set (Table 8) it was necessary to obtain DNA segments lacking all of the 72 sites. Fragments of ~1000 bp are statistically unlikely to occur even in the human genome, and also difficult to search for. Hence, fragments of ~500 bp were identified, since these are several orders of magnitude more common in human DNA. Thus, to generate the 1000 bp spacer segments, pairs of 500 bp fragments can be amplified by PCR from a human BAC clone, ligated together, and inserted between the polylinkers of the pDM1–4 plasmids. These can be ligated and inserted into the restriction site-free positions of the backbone of the pDM1–4 set during construction.

Identifying Suitable Spacer Fragments

Any nucleic acid sequence which contains none of the restriction sites represented in the polylinker regions of the plasmid may be used for the restriction site-free region. The following DNA fragments are examples of suitable restriction site-free segments for practicing the method of the present invention and have been derived from chromosome V of the human genome. Each was chosen by a procedure, as described below, which locates fragments lacking any of the 64 possible 6 bp palindromes. The "Gene Construction Kit" software was used to locate each of the possible standard 6 bp non-degenerate palindromic restriction sites (i.e. all 64 6 bp palindromes) in the 134,336 bp sequence contained in the BAC plasmid CIT-HSPC_235N17. The resulting list of sites, numbered by position in the sequence were imported into EXCEL. The distances between sites were then listed in the Excel spread-sheet as fragments, ordered by size, and identified by positions in the sequence (from 1 to 134,336). The largest eight sequences are listed below, ranging from 459 to 639 bp.

```
72394-73038
TATATAAAAATAATAATGTTTTTACTTTTTTAAGTATTGGAAGTACCTTAGAAATCATTGACTTTG    (SEQ ID NO.1)

CCCAACTGCCCCATTTTACAGTTGTGGAAACCGAGGTCATAGAATTGGTAAATTACGAAGAAAACT

GTGTTTCCTAGTAGGTCTCCCTGCCTTCACTCTGCCTCCACCACCAGGAGTCTCTGCACCCAGTCA

TCTTTCTAAGGGGTGTGCCATCCATCACTCCCCACGCAAAACCTCTCTGTGCCCTCCAATGCAGCT

AGACTGAAGCCTGTGATGTCAGTGTGGTCAGATCCCTGCAACCTCAGCTTGTGTTCATGGCACACT

GTGCTTCTGCTACCCTGGCCTTCTCTCTGCTGTGTGAACACACTAAGGTTTAACCCTTCCCGTTGT

CTTGGAGGGAAATTCTCCCAGATATTCAGGCTTCTTTGTGTCATTCAGTCTCACTCAGCTCAAAA

GGGCACTTCCTCTGGGCTGCCCTAACCCCCACCAGACACCCAAACTAGATGCACAACGCTCGTCAC

TCTTTCCCATCAGCCTGATTGGATGCCTCTAAAGCATGTACCACTATCTGTACCACTGCTCATTTA 133197-133749
AAGCTTTTAAGACAGAATCATAGACCATAAAACTATTTAATAAGTACAATGTACTAAAAATATCCT    (SEQ ID NO.2)

TTACTGAGACAGATTGGTGAATTAAAGAGCACCAGCTTAAAAAGATCAGGAAGCCAGATGCTGTTC

TCTGCTCAGGCCCAGCCTCAATCATGTGGCCCTGGGCAGGCACCTCCTCAACTTGACCTCAGTTTT

GCCCTTTTTACAATGGTATCTATAAGTTCTTCTTGGCTCTGCTATTCTGGAATTATCTTATGTAGA

ATAAGTCTTCCCAAGCTGTGTGGGGCTTTTCCTGGTAGATTTGAGGGAAGTTTTGTTCTGTTTTGT

TTTATTGTTTGCTTACCCTGCTACTGCCAGTGAAGTCAACACTACAAGCAGACAGTAAGCCAGGAA

ACATTTCTCCCTGTCAGGTCAGCACATCCCATTAGGTGGATCTGGTGCTCAAGTTTATTAGATCAG

GAGACCGATGCTGGGGAAGGCTCACAGAGTGGTCTGAGTCAGTTGCTCTACCATGAGGTTGGAGTG

TAGTAGATTCAACATCCTGTGTACA
```

-continued

75726—76260
TCATGAGGTCAGGAGATTGAGACCATCCTGGCTAACACGGTGAAACCCCATCTCTACTAAAAATAC (SEQ ID NO.3)

AAAAAAATTAGCCGGGCGTGGTGGTGGGCACCTGTAGTCCCAACTACTCGGGAGGCTGAGGCAGGAG

AAATGGCATGAACCTGGGAGGCAGAGCTTGCAGTGAGCCTCAGATTGCACCACTGCACTCCAGCCTG

GGCAACAGAATGAGACTCCATCTCAAAAAAAAAAAAAAAACAACTTGTCCAAGTTTATATGGCCTGG

TACAGGCAGGATTTAGGCAACTGAATCCACAGGTGCTGCTGAACCACCAGGAGATCCTGCTGCCCAA

GTAACTGCAAAACGGGGCACCAGGGACTGTCTAGGACCACAGGTCGAGTTCCACCTCTGCCAACCTA

GTTTGTTAGCCCTTCCTTCCTTCCTTCCTTCCTCCTTCCTTTTCTTGTTCTTGCCTGCCAGCT

TTCCTCTTTCTACATTTCTTCCTCCTCCTTCCTTCTCTCTGTCTCTTCTATCCTACATTAAGTATA

AGTTTTTCATGA

94154—94684
CTGCAGCAGGCATCTCTTGGTGCCATGAGTCCTGGTGGGCCTTATTGATTCCTTATTCATTTCTTA (SEQ ID NO.4)

TCACCCCATGTGAATCAGATTCAGTTGCTTCACATTTTCTTCACTGCTCTTATCACTGCCCGATAT

TATATTACAGTTGTGAGTTTTGCACCTCTTATATTAAGACAGTGTCTGCCACATAGTAAGCACTTA

GTATTTGCTGAAAGTTGTAAAAGTGCATCAATGAGTATCCCACAGTGCCGGGCACATAATAGATAT

TCCATAATTGTTGTAAAATAGCATTTCCTCTCTGTCCAGGGAACAGGGATGGGAGGGTGGTATAAT

GGGGAGCATTTTGTTCAGGGATGTTTTCTGGATGTGGCATTTGAGCTAGACCTTAAAAGATGGAGT

ACAATTCCACAAGGAAGGCTTAGTAGTTGGGCATTCCAAACAAAAAGGACAGGTGTTTAGACATGG

AAAGCATTAGGGGACATTTGAGAATTTGGGAATAGCTCAGTTTAGCTGGCAGACTGGAATACAAAG

AGGAATTC

111084—111592
AGTACTTATTACATTTTAGGTCTTATTTAATTGTCTGTGTTCCTCTCCATTCCCACCAACTAGGGC (SEQ ID NO.5)

CTGACACATAGGGGTTCAATAATTGTCAAGTGATTGACAGAATGAATGAATGGATGGATGAGTGAA

AAAGTCTCTCCATTTCCAGTGTGTATTCTCTAATATCTTCTACATTCTACACTGAAATTGTCTT

TTTGAAGCCTGGGACTTCTTCAGTGGCTTGTCATTGCCAGTGGATAAAATGCAGACTTTTCATCTG

TGCATTCAAGAACTACCACATATAGTCTCAGCCTACCATTTCTCTTTTTTTTTTTTTAGATGGA

GCCTTTCTCTGCTGCCCAGGCTGGAGTGCAGTGGCATGGTCTCGGTTCACTGCAACCTCTGCCTGT

TGGGTGCAAGAGATTCTCCTGCCTCAGCCTCCTGAGTAGCTGGGATTACAGGCACCCACCACCACA

CCCAGCTAATTTTTGTATTTTTAGTAGAGATGGAGTTTCACCATGTTGGCCA

76528—77029
GAATTCATGTTAATCCACATAGAGAATTGAGAGATCAGAGCCTTCAATAAATGCCAACCAACATTT (SEQ ID NO.6)

ACAGTGTATTGTCTGTCAGCACAGTGCTGTGACAGTGCTGGGGATAAAACAACACAGACGCCAGGG

CATCAGACCCTACCCCCACGGTTGCTTTATGTACTCTCAGGGCACAGGGACGCTTTCATTCTGTGC

TCTTATCACACTGACTTGTGTCATCTCTTGACTGTCAGTCTCTCCCACTGAACTACAAACCTTTTG

AGAGCAGAAGCCCTTTTTCTTTTATTGTTTTCTCAGCATTTCATATCCTATTGCACAAATCAGGAC

TTGGCACATATAGATGCTCCATAAAGTAAATGGTTGAATTGAATAAAATACATAGTACCCCGTATT

AGTTTGCTAGGGCTTCCATAACAAATACCACAGCCTGGGTGGCTTACACAATGGAATTTTTATTTT

CTCATGGTCTTGGAGGCTGGAAGTCCAAGATCAAGGTGCCTGCAG

36677—37159
AAATTTACGCGAAGCAGGATACAGAAAGCAGCCAGAAGTGGAGCAGCACCAGCCGGGGTGGGGAC (SEQ ID NO.7)

CAAGACCTCCCACCCTCCTTGGTGTCTGTCTGCCTTTTGAGGTCCCTCTGCCAAGTGGCGCTCTGC

TGAGCAAGTAATCCCTCAGGGCACTCCAACTCTGAGACAGAATGATTTATAGCCCTGTTAATCCAA

CCAGGCTGTCAAAAACGGCCACATCAGCAGACATACACAGAGACATGCAGTCACATACACTCAGGA

-continued

CAAAAAATAAGCCCCAGAAACTGCTTGAGCAAGCTCAGGCTTTTCTCTAGCACCTTCCTCATTTGT

TCAAGTTTTTGCCATCTTTATTTTCATTTCCTGGTTTCTTCTCACATCCTTCCTCTTTTCCCCTCC

AAGTTACTAAAAATTCTAACAATTTCTACTTTTACTTCTTTGTTGTTATCTGCGGCACATCGTTGC

CCCACCCCCACTCTTGGTCGCTATAG 89707-90178
TTGCAAAGCTGGAGACCCAGAAAAACTGATAATGTAGTACAAGTCCAACATTGGCAGACTTGAGAC (SEQ ID NO.8)

CTGGGAAGAGCCAATGTTTTAGTTTAAGTCTGTCAGTAAAAAGAAACCAATGTGCCAGCTCAAAGG

CAGACAAAGCATGGGAATTTTCTATTATAGGGAGGAAGGTCAGCCTTTTTTCCTATTCAGGTCTTC

AATGGATTGGACGGGAACCATCCACATTAGGGAGGGCAATCTGCTTTACTTAGTCTCCCCAATCAA

ATGTTAATCTCATCCAGAAATATCAGCACACACAACCTTAGAATAATGTCTGACCAAATGTCTGGG

CACCCAATAGCTCAGTCAAGTTGACACATAAATTAACCATCACTTGGCCGGACGCTGTGGGCTCAC

ACCTGTTATCCCAGCACTTTGGGTGGGTGGATCACCTGAGGTTCCTTAGGAATGTAAAGAGGTGAG

CACTTAGAATCTAGA 5757-6216
AAAGCTTACAACTTGCTGGTGCTGTTTCCTGGGATTTACTCCCTGCTCTGGAGTATCTCTAACCTT (SEQ ID NO.9)

TGGAGGTGCTACCACATGCCCCACCCTCACCCCAGGTTTTGATGACCACCCCATCTTTTAGGAGTT

CCCCTTATTTTTATATCCTCATCCTTTCTCTATCCATGCTCAGTCATGGTCAATGTGAAATCTGTG

CTGTGGCTTTCCTGGCTTGGCTCTTTCATAGATAAACCTATAAGCCAAGATTTGAGAAATCTTTCT

CTCTCTCTCTCTCTCTCTCTCTCTCTCAAATAAGTTGGTGTTCTTTTTTTTTCTTTAGCAA

ATTGGCAACATTTCCTATCAGATTATGTATTGTTTCACAGGCTATACAACTCTAGGAACTATCAGG

GGTTATTTGGAAGAAAAACAACTGGTGTACTATTTTTCTAATACTACACCTACAAAAACATCCAAT

ATT

Once suitable restriction site-free sequences have been identified, two or more may be ligated, using techniques well known to those of skill in the art, to obtain a single site-free sequence of the appropriate length, that is, at least about 15% of the length of the completed plasmid, to separate the polylinker regions of the plasmid. A plasmid that is around 4 kb will, therefore, contain restriction site-free regions at least about 600 bp in length.

EXAMPLE 1

In one embodiment, a set of four digestion monitor plasmids, referred to herein as $pDM_y1-4$, as shown in Table 9, was constructed as follows.

The region between polylinkers 1 and 3 corresponds to the segment of pUC19 between the SspI and HindIII sites, containing the origin of replication and the ampicillin resistance gene (nt 474 to 2501, 2.03 kb). The regions between polylinkers 1 and 2 and polylinkers 2 and 3 are segments from the S. cerevisiae genome corresponding to chromosome V, nt 108955–109978 and nt 104477–105368 (1.02 and 0.89 kb respectively). The plasmids also comprise three polylinker segments of about 50–60 nt each, as described.

Construction of $pDM_y1$ pUC19 was linearized with Ssp I and Hind III, end-filled with Klenow polymerase and ligated to oligo RSB (see Table 10 below) to generate pUC-RSB. PCR fragments were amplified from two regions of Chromosome V (fragment A: nt108955 to nt109978; fragment B: nt104477 to nt105368) using the oligos 1080-5' and 1080-3' and 898-5' and 898-3' (Table 10) Fragments A and B were digested with EcoRI and SalI and SalI and BamHI respectively and inserted successively into the corresponding sites in pUC-RSB to generate pDCMa. An unexpected MfeI site (i.e. one not present in the published SGD sequence was found in the B fragment and eliminated by digesting with MfeI followed by end-filling with Klenow and religating to generate pDCM. This plasmid was digested with Eco RI and Hind III and ligated to the p1-1 oligo, generating $pDM_y1-1$. $pDM_y1-1$ was cut with Sal I and Bgl II and ligated to the p1-2 oligo generating $pDM_y1-1,2$. $pDM_y1-1$ was digested with Xho I and Bam HI and ligated to the p1-3 oligo, generating $pDM_y1-1,3$. $pDM_y1l-1,2$ and $pDM_y1-1,3$ were each digested with Eco RI and Bgl II; the fragment containing the vector backbone of pDM1-1,3 was ligated to the 1 kb EcoRI-BglII fragment of $pDM_y1-1,2$, generating $pDM_y1a$. An unexpected NdeI site in fragment B was eliminated by partial digestion with NdeI followed by Klenow end-filling and religation, generating $pDM_y1$.

Construction of $pDM_y4$

To create $pDM_y4$, pDCM was cut with Eco RI and Hind III and ligated to the p4-1 oligo, generating pDMy4-1. $pDM_y4-1$ was digested with Sal I and Bgl II and ligated to the $pDM_y4-2$ oligo. The resulting $pDM_y4-1,2$ was then cut with Bam HI and Xho I and ligated to the p4-3 oligo generating $pDM_y4a$. The unlisted NdeI site was eliminated as described above, generating $pDM_y4$.

Construction of $pDM_y22$

To create $pDM_y2$, $pDMY_y1$ was cut with Eco RI and Spe I and ligated to the p2-1 oligo, generating $pDM_y2$ 1. This plasmid was digested with Sal I and Pst I and ligated to the p2-2 oligo, generating $pDM_y2-1,2$. This plasmid was partially digested with XhoI, then fully digested with NheI and ApaI and ligated to the p2-3 oligo. A plasmid isolate containing the oligo inserted at the correct position was identified and designated pDM$_y$2.

Construction of pDM$_y$3

To generate pDM$_y$3, pDM$_y$2 was digested with Nco I and Bam HI and ligated to the p3-3 oligo, generating pDM$_y$3-3. This plasmid was digested with Bgl II and Mlu I and ligated to the p3-2 oligo, generating pDM$_y$3-2,3. This plasmid was partially digested with Hind III, then fully digested with Ngo MIV and ligated to oligo p3-1. A plasmid isolate with the oligo in the correct position was identified and designated pDM$_y$3-1,2,3-XbBg. To eliminate a superfluous XbaI site remaining from the earlier stages the plasmid was partially digested with XbaI, end-filled with Klenow and religated. A plasmid isolate containing a single XbaI site in the correct position was was identified and designated DM$_y$3-1,2,3-Bg. To replace a superfluous BglII site with an NruI site this plasmid was partially digested with BglII and ligated to the Bgl IIx-Nru oligo. A plasmid isolate containing a BglII site in the correct position was identified and designated pDM$_y$3.

The sequence of each of the three multiple restriction site regions in each plasmid was confirmed by Sanger sequencing.

TABLE 10

Oligonucleotides used in construction of pDM$_y$1-4

| | | |
|---|---|---|
| RSB+ | gaattcaaaagtcgacaaaaggatcc | (SEQ ID NO.10) |
| RSB- | ggatccttttgtcgacttttgaattc | (SEQ ID NO.11) |
| 1080-5' | gagagaattctataaagcttcgtattccaatggggagc | (SEQ ID NO.12) |
| 1080-3' | gagagtcgacagaaaacattctctagggattacg | (SEQ ID NO.13) |
| 898-5' | gagagtcgactataagatctccataccattgtagtattgactactaactac | (SEQ ID NO.14) |
| 898-3' | gagaggatcctatactcgagtagaaaaccagattttgcctc | (SEQ ID NO.15) |
| p1-1+ | agcttaagcatgcggccgccggcggtaaccggtaccactagttcg | (SEQ ID NO.16) |
| p1-1- | aattcgaactagtggtaccggttaccgccggcggccgcatgctta | (SEQ ID NO.17) |
| p1-2+ | gatctgtctagacgcgtatcgatatcaattgaggcctgcagctgttaac | (SEQ ID NO.18) |
| p1-2- | tcgacgttaacagctgcaggcctcaattgatatcgatacgcgtctaaaagaca | (SEQ ID NO.19) |
| p1-3+ | gatcctaggcgccatggccagctagcccgggcccatatgagc | (SEQ ID NO.20) |
| p1-3- | tcgagctcatatgggcccgggctagctggccatggcgcctag | (SEQ ID NO.21) |
| p2-1+ | ctagctgcagctgttaacgtcgac | (SEQ ID NO.22) |
| p2-1- | aattgtcgacgttaacagctgcag | (SEQ ID NO.23) |
| p2-2+ | tatgagctcgaga | (SEQ ID NO.24) |
| p2-2- | tcgatctcgagctcatatgca | (SEQ ID NO.25) |
| p2-3+ | ctagcccgggcccactagttcgaat | (SEQ ID NO.26) |
| p2-3- | tcgaattcgaactagtgggcccggg | (SEQ ID NO.27) |
| p3-1+ | agctagatctgtctagacgcgtcatg | (SEQ ID NO.28) |
| p3-1- | acgcgtctagacagatct | (SEQ ID NO.29) |
| p3-2+ | gatcggatcctaggcgc | (SEQ ID NO.30) |
| p3-2- | cgcggcgcctaggatcc | (SEQ ID NO.31) |
| p3-3+ | gatcaagcttaagcatg | (SEQ ID NO.32) |
| p3-3- | cgcatgcttaagctt | (SEQ ID NO.33) |
| p4-1+ | agcttaccggtctagagctcaattggccacccgggccctaggcctgcag | (SEQ ID NO.34) |
| p4-1- | aattctgcaggcctagggcccgggtggccaattgagctctagaccgaaa | (SEQ ID NO.35) |
| p4-2+ | gatcttaagtatcgatgccggcgccatggtaaccatatgttaactag | (SEQ ID NO.36) |
| p4-2- | tcgactagttaacatatggttaccatggcgccggcatcgatacttaa | (SEQ ID NO.37) |
| p4-3+ | tcgagatatcacgcgttcgaagctagcggccgcatgcggtaccagctg | (SEQ ID NO.38) |
| p4-3- | gatccagctggtaccgcatgcggccgctagcttcgaacgcgtgatatc | (SEQ ID NO.39) |
| Bgl$_x$-Nru | gatcgtcgcgac | (SEQ ID NO.40) |

Maintenance and Replication of Plasmids

The plasmids of the present invention additionally comprise a selectable marker and bacterial origin of replication. The plasmids are replicated by growth of *E. coli* cells which have been transformed with the plasmid by standard techniques. Growth conditions are in standard growth medium, for example, Luria Broth, containing the antibiotic for which the plasmid contains a resistance gene, usually, but not limited to, ampicillin. After cell harvest, plasmid DNA is purified by standard plasmid DNA preparations, for example, Qiagen (Valencia, Calif.) or Sigma (St. Louis, Mo.) miniprep techniques. Plasmids in solution are stored frozen or in a dry (lyophilized) state. Cells carrying plasmids are stored frozen in growth media or on agar plates at 4° C.

Use of pDM Digestion Monitors

Figure 3:
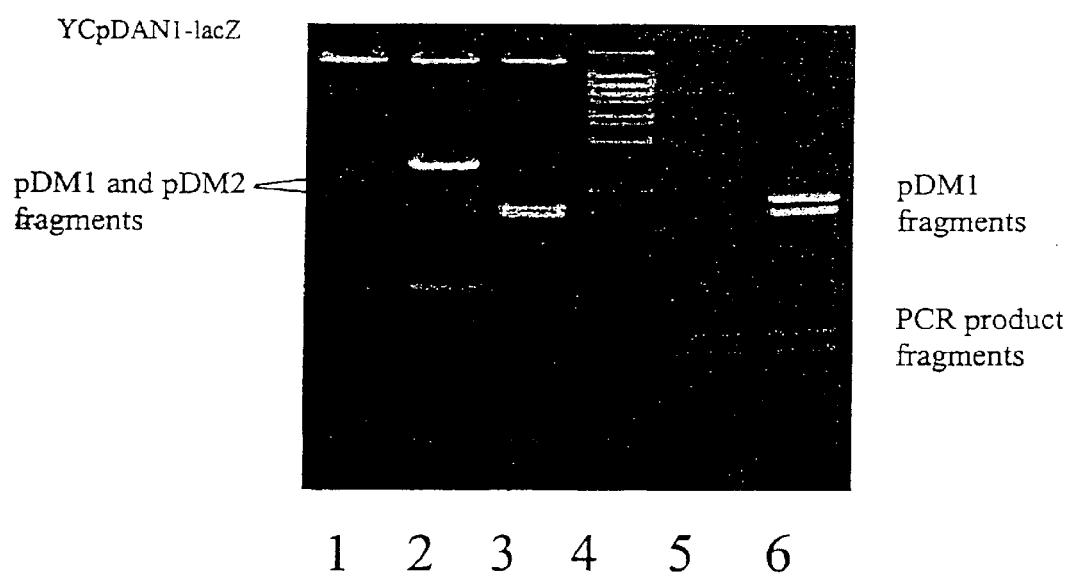
FIG. 3 is a photograph of an ethidium bromide stained 1% agarose gel.

DNA samples were digested with pairs of restriction enzymes in accordance with known techniques, alone and in the presence of pDM digestion monitors, and run on a 1% agarose gel. The results are shown in FIG. 3. Lane 1 contained plasmid YCpDAN1-lacZ alone digested with EcoRI and SalI. The 12 kb plasmid contains an EcoRI and SalI site separated by 500 nucleotides The 12 kb plasmid is not, therefore, readily resolved from 11.5 kb. Lane 2 contains the same but includes pDM1. Lane 3 contains the same digestion reagents plus pDM2. In this sample, the pDM2 fragments run as a doublet. λ phage DNA digested with BstEII was run in lane 4 as a molecular weight marker. A PCR fragment amplified from yeast ANB1 gene was run in Lane 5. This fragment contains an internal EcoRI site and a HindIII site at the 5' end contained in the primer. The PCR product was digested with EcoRI and HindIII. Lane 6 contains the same sample as Lane 5 with pDM1 added. As shown by FIG. 3, the absence of linear pDM indicates double digestion.

Linear Monitors

The digestion monitor plasmids of the present invention can be used in linear form. The advantage of this format is that, in cases where one of the enzymes being tested fails to cut, it can be determined which one isn't working simply by inspecting the gel pattern. To linearize the plasmid, a restriction site having a position far enough from the midpoint of the backbone to permit discrimination of gel migration patterns is chosen. So, for example, in one embodiment, the plasmids of the present invention are supplied pre-digested with BglI. BglI is chosen because the position of the unique BglI site is sufficiently far from the midpoint of the backbone to permit this discrimination.

The following illustration depicts a plasmid containing restriction sites BglI, A, B and C. The plasmid has been linearized by digestion with BglI.

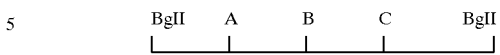

When the linearized plasmid is cut at sites B and C, the following fragments are obtained:

If, however, the B enzyme fails to cut, the resulting products would be:

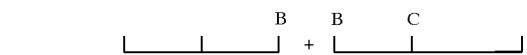

Similarly, if the C enzyme fails to cut, the resulting fragments are:

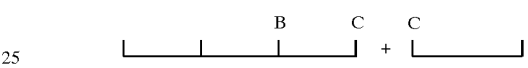

The migration pattern of the two pairs of digestion products are easily distinguishable by gel electrophoresis, thereby indicating not only that the reaction was incomplete but also providing specific information with respect to which enzyme failed.

The present invention also provides a kit for monitoring the efficiency of an endonuclease digestion. The kit includes one or more plasmids containing restriction sites of utility to the molecular biologist and instructions for use of the plasmids to monitor the efficiency of a digestion using the endonucleases whose sites are represented on the monitor plasmid. The instructions may include, in part, a table or chart, for example, one similar to that shown in FIG. 4, which indicates the plasmid that will be informative for the two restriction endonucleases to be used. A dot at the intersection of two sites indicates pairs of restriction endonucleases for which none of the plasmids is informative, for example, where the two sites are linked and therefore, are in the same polylinker in each of the four plasmids.

In another embodiment, the monitor plasmids might be supplied together with restriction endonucleases, and suitable reaction buffers, for the purpose of providing the purchaser with a means for testing the activity of enzymes in different combinations.

What is claimed is:

1. A set of plasmids for use in monitoring the efficiency of a restriction endonuclease digestion, wherein each of said plasmids of the set comprises:
   a) at least one spacer segment comprising a nucleic acid sequence that is restriction site-free; and
   b) at least two polylinker regions, wherein each of said polylinker regions contains a plurality of unique restriction sites which are present on each of the plasmids of the set and wherein said restriction sites are distributed so that for any two restriction enzymes whose sites are represented on the plasmids, the two sites will be in separate polylinkers on at least one of the plasmids of the set and wherein digestion of that plasmid of the set with the two restriction endonucleases results in two fragments, said fragments being sufficiently different in size from the intact plasmid so as to be readily distinguishable from said plasmid.

2. The set of claim 1 wherein the size of one of said fragments is at least about 15% less than the intact plasmid.

3. The set of claim 1, wherein the length of said spacer segment is about 20–85% of the length of the plasmid.

4. The set of claim 1, wherein the length of said spacer segment is about 30–85% of the length of the plasmid.

5. The set of claim 1, wherein the length of said spacer segment is about 40–85% of the length of the plasmid.

6. The set of claim 1, wherein the length of said spacer segment is about 50–85% of the length of the plasmid.

7. The set of claim 1, wherein digestion of any plasmid of the set with two endonucleases whose recognition sites are represented on said plasmid results in two fragments, one of said fragments being at least about 15% of the length of the undigested plasmid.

8. The set of claim 1, wherein each plasmid of the set further comprises a replication origin and a selectable marker.

9. The set of claim 1 wherein said plasmid is linearized prior to use in an endonuclease digestion reaction.

10. The set of claim 1, wherein the set comprises $pD_yM1$, $pD_yM2$, $pD_yM3$ and $pD_yM4$.

11. The set of claim 1, wherein the set comprises pDM1, pDM2, pDM3 and pDM4.

12. A set of plasmids for use in monitoring the efficiency of a restriction endonuclease digestion, wherein each of said plasmids of the set comprises:
   a) at least one spacer segment comprising a nucleic acid sequence that is restriction site-free; and
   b) at least two polylinker regions wherein each of said polylinker regions contains a plurality of unique restriction sites distributed so that, for any two sites, the two sites are situated within different polylinker regions on at least one plasmid of said set and wherein said polylinker regions are separated by the spacer segment of a) whose length is about 15–85% of the length of the plasmid.

13. The set of claim 12, wherein the length of said spacer segment is about 20–80% of the length of the plasmid.

14. The set of claim 12, wherein the length of said spacer segment is about 30–80% of the length of the plasmid.

15. The set of claim 12, wherein the length of said spacer segment is about 40–80% of the length of the plasmid.

16. The set of claim 12, wherein the length of said spacer segment is about 50–80% of the length of the plasmid.

17. A method for designing a plasmid for use in monitoring the efficiency of a restriction endonuclease digestion comprising:
   (a) identifying at least one spacer segment comprising a nucleic acid sequence that is restriction site-free;
   (b) identifying a plurality of restriction sites to be represented on said plasmid;
   (c) assigning each of said restriction sites to a polylinker region on said plasmid such that for any two restriction sites, the two sites are situated in different polylinkers;
   (d) distributing said polylinker regions on said plasmid such that said polylinker regions are separated by a spacer segment at least about 15%–85% of the length of the plasmid.

18. The method of claim 17 wherein digestion of said plasmid with any two endonucleases represented on said plasmid results in two fragments, one of said fragments being at least about 15%–85% of the length of the intact plasmid.

19. A method for designing a set of plasmids for use in monitoring the efficiency of a restriction endonuclease digestion comprising:
   (a) identifying at least one spacer segment comprising a nucleic acid sequence that is restriction site-free;
   (b) identifying a plurality of restriction sites to be represented on said plasmids;
   (c) assigning each of said restriction sites to a polylinker region on one of said plasmids such that for any two restriction sites, there is at least one plasmid in the set in which the two sites are situated in different polylinkers;
   (d) distributing said polylinker regions on said plasmids such that said polylinker regions are separated by a spacer segment at least about 15%–85% of the length of the plasmid.

20. A method for designing a set of plasmids for monitoring the efficiency of a restriction endonuclease digestion comprising:
   (a) identifying at least one spacer segment comprising a nucleic acid sequence that is restriction site-free;
   (b) identifying a plurality of restriction sites to be represented on said plasmids;
   (c) determining the number of polylinker regions (a) that will accommodate said restriction sites, wherein the maximum number (N) of sites which can be represented is $N=a^b$, where a is the number of polylinkers in each plasmid, b is the number of plasmids in the set; and
   (e) assigning each of said restriction sites to a polylinker region in accordance with a template, wherein said template corresponds to an a×b matrix, and wherein each of said sites is in a different polylinker from any of the other sites in at least one of the plasmids in the set.

21. A set of plasmids obtained by the method of claim 20.

22. The set of plasmids of claim 21 further comprising additional restriction sites situated in vector cloning sites of the plasmids.

23. A method for designing a set of three plasmids for monitoring the efficiency of a restriction endonuclease digestion comprising:
  (a) identifying at least one spacer segment comprising a nucleic acid sequence that is restriction site-free;
  (b) identifying 27 restriction sites to be represented on said plasmids;
  (c) numerically ordering said restriction sites;
  (d) assigning each of said restriction sites to a polylinker region, wherein
    (i) sites 1–9 are assigned to a first polylinker on a first plasmid, sites 10–18 are assigned to a second polylinker on said first plasmid and sites 19–27 are assigned to a third polylinker on said first plasmid;
    (ii) sites 1, 4, 7, 10, 13, 16, 19, 22 and 25 are assigned to a first polylinker on a second plasmid, sites 2, 5, 8, 11, 14, 17, 20, 23, and 26 are assigned to a second polylinker on said second plasmid and sites 3, 6, 9, 12, 15, 18, 21, 24, and 27 are assigned to a third polylinker on said second plasmid;
    (iii) sites 1, 2, 3, 10, 11, 12, 19, 20 and 21 are assigned to a first polylinker on a third plasmid, sites 4, 5, 6, 13, 14, 15, 22, 23 and 24 are assigned to a second polylinker on said third plasmid and sites 7, 8, 9, 16, 17, 18, 25, 26 and 27 are assigned to a third polylinker on said third plasmid; and
  (e) distributing said polylinker regions on each of said plasmids such that said polylinker regions are separated by a spacer segment at least about 15% of the length of the plasmid.

24. A set of plasmids constructed according to the method of claim 23.

25. The set of plasmids of claim 24 further comprising additional restriction sites situated in vector cloning sites of the plasmids.

26. A method of constructing a set of four plasmids for monitoring the efficiency of a restriction endonuclease digestion comprising:
  (a) identifying at least one nucleic acid sequence that is restriction site-free;
  (b) identifying 64 restriction sites to be represented on said plasmids;
  (c) numerically ordering said restriction sites;
  (d) assigning each of said restriction sites to a polylinker region, wherein
    (i) sites 1–16 are assigned to a first polylinker on a first plasmid, sites 17–32 are assigned to a second polylinker on said first plasmid, sites 33–48 are assigned to a third polylinker on said first plasmid and sites 49–64 are assigned to a fourth polylinker on said first plasmid;
    (ii) sites 1–4, 29–32, 41–44 and 53–56 are assigned to a first polylinker on a second plasmid, sites 5–8, 17–20, 45–48 and 57–60 are assigned to a second polylinker on said second plasmid, sites 9–12, 21–24, 33–36 and 61–64 are assigned to a third polylinker on said second plasmid and sites 13–16, 25–28, 37–40 and 49–52 are assigned to a fourth polylinker on said second plasmid;
    (iii) every fourth site beginning with site number 1 is assigned to a first polylinker on a third plasmid, every fourth site beginning with site number 2 is assigned to a second polylinker on said third plasmid, every fourth site beginning with site number 3 is assigned to a third polylinker on said third plasmid; and every fourth site beginning with site number 4 is assigned to a fourth polylinker on said fourth plasmid.
  (e) distributing said polylinker regions on each of said plasmids such that said polylinker regions are separated by a restriction site-free region at least about 15% of the length of the plasmid.

27. A set of plasmids constructed according to the method of claim 26.

28. The set of plasmids of claim 27 further comprising additional restriction sites situated in vector cloning sites of the plasmid.

29. A kit for monitoring the digestion efficiency of a restriction endonuclease digestion reaction comprising:
  (a) a set of at least two plasmids wherein each of said plasmids contains a plurality of unique restriction sites which are present on each of the plasmids of the set and wherein said restriction sites are distributed so that for any two restriction enzymes whose sites are represented on the plasmids, the two sites will be in separate polylinkers on at least one of the plasmids of the set and wherein digestion of at least one of said plasmids with any two restriction endonucleases represented on the plasmid results in two plasmid fragments, one of said fragments being at least about 15% of the length of the undigested plasmid; and
  (b) instructions for choosing the plasmid of the set which will be informative for digestion with the two restriction endonucleases.

30. The kit of claim 29, wherein the kit comprises two plasmids.

31. The kit of claim 29, wherein the kit comprises three plasmids.

32. The kit of claim 29, wherein the kit comprises four or more plasmids.

33. The kit of claim 29, further comprising restriction endonucleases for sites represented on said plasmids.

34. The kit of claim 33, further comprising appropriate buffers for the restriction endonucleases represented on said plasmids.

* * * * *